(12) United States Patent
Tanaka

(10) Patent No.: US 9,241,394 B2
(45) Date of Patent: Jan. 19, 2016

(54) RADIATION IMAGING CONTROL APPARATUS AND METHOD FOR CONTROLLING THE SAME

(71) Applicant: CANON KABUSHIKI KAISHA, Tokyo (JP)

(72) Inventor: Hikaru Tanaka, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 402 days.

(21) Appl. No.: 13/914,839

(22) Filed: Jun. 11, 2013

(65) Prior Publication Data

US 2013/0336456 A1 Dec. 19, 2013

(30) Foreign Application Priority Data

Jun. 15, 2012 (JP) ................................ 2012-135829

(51) Int. Cl.
| | |
|---|---|
| *H05G 1/30* | (2006.01) |
| *G01N 23/04* | (2006.01) |
| *G06F 19/00* | (2011.01) |
| *A61B 6/00* | (2006.01) |

(52) U.S. Cl.
CPC ................. *H05G 1/30* (2013.01); *A61B 6/467* (2013.01); *A61B 6/548* (2013.01); *G01N 23/04* (2013.01); *G06F 19/3406* (2013.01); *A61B 6/405* (2013.01); *A61B 6/4233* (2013.01); *A61B 6/545* (2013.01)

(58) Field of Classification Search
CPC ...... A61B 6/405; A61B 6/4233; A61B 6/467; A61B 6/545; A61B 6/548; A61B 6/032; A61B 6/542; A61B 6/4291; A61B 6/484; A61B 6/4441; A61B 6/54; A61B 6/06; A61B 6/4452; A61B 6/502; A61B 6/56; A61B 6/4464; A61B 6/4021; A61B 6/00; A61B 6/4283; A61B 6/4405; A61B 6/563; A61B 6/544; A61B 2560/0214; A61B 6/465; A61B 6/504; A61B 6/5205; A61B 6/5235; A61B 6/586; A61B 5/055; A61B 6/44; G01N 23/04; G06F 19/3406
USPC .................................................. 378/4, 15, 91
See application file for complete search history.

(56) References Cited

U.S. PATENT DOCUMENTS

| | | | | |
|---|---|---|---|---|
| 7,139,368 | B2* | 11/2006 | Kawanabe | A61B 6/032 378/162 |
| 7,693,252 | B2* | 4/2010 | Noshi | A61B 6/00 378/4 |
| 2003/0076919 | A1* | 4/2003 | Suzuki | A61B 6/542 378/4 |
| 2003/0099323 | A1* | 5/2003 | Nagata | A61B 6/032 378/4 |
| 2008/0056547 | A1* | 3/2008 | Kokubun | A61B 6/032 382/128 |

FOREIGN PATENT DOCUMENTS

| | | |
|---|---|---|
| JP | 2002200062 A | 7/2002 |
| JP | 2005110844 A | 4/2005 |
| JP | 2006218142 A | 8/2006 |

* cited by examiner

*Primary Examiner* — Irakli Kiknadze
(74) *Attorney, Agent, or Firm* — Canon USA Inc. IP Division

(57) ABSTRACT

A radiation imaging control apparatus configured to control a radiation imaging operation using a radiation generation apparatus in which a radiation generation condition is adjustable by a manual operation includes a setting unit configured to set the radiation generation condition for the radiation imaging operation, a transmission unit configured to transmit the radiation generation condition to the radiation generation apparatus, and a transmission control unit configured to limit transmission of the radiation generation condition by the transmission unit in a case where a radiation imaging operation belonging to the same group as that of the radiation imaging operation is performed.

9 Claims, 20 Drawing Sheets

RADIATION IMAGING CONTROL APPARATUS AND METHOD FOR CONTROLLING THE SAME

BACKGROUND OF THE INVENTION

1. Field of the Invention

The present invention relates to a radiation imaging control apparatus configured to reduce an operator's load for adjusting protocol information so as to be suitable for a patient for every imaging operation when performing a plurality of radiation imaging operations, and a method for controlling the radiation imaging control apparatus.

2. Description of the Related Art

In recent years, a digital X-ray system has become widespread, which irradiates a flat panel detector (FPD) with X rays from an X-ray generation apparatus, reads the X rays transmitted through a patient using the FPD, and transmits an image to an X-ray imaging control apparatus from the FPD to provide an X-ray imaging image to an operator.

In conventional techniques discussed in Japanese Patent Application Laid-Open Nos. 2002-200062, 2005-110844, and 2006-218142, an X-ray imaging control apparatus transmits protocol information including a radiation generation condition such as intensity of X rays irradiated from an X-ray generation apparatus and an irradiation time to an X-ray generation apparatus previous to an X-ray imaging operation, to arrange the protocol information between the X-ray generation apparatus and an FPD using the protocol information previously set in the X-ray imaging control apparatus.

An operator changes the protocol information in the X-ray generation apparatus, and the X-ray generation apparatus notifies the protocol information to the X-ray imaging control apparatus, which can change the protocol information between the X-ray generation apparatus and the FPD.

When the operator changes the protocol information, the operator finely adjusts the protocol information in consideration of the body type, imaging target region, and target region direction of an imaging patient subjected to the X-ray imaging operation, and performs the X-ray imaging operation using the protocol information suitable for the patient.

However, when the operator transmits the protocol information previously set in the X-ray imaging control apparatus for every X-ray imaging operation to the X-ray generation apparatus previous to the X-ray imaging operation as described above, a reset function acts in a general X-ray imaging apparatus, and a numerical value adjusted by the operator for a first imaging operation is reset for a second imaging operation. Therefore, even when the protocol information in the first imaging operation is the same as that in the second imaging operation, the operator is required to re-perform adjustment.

SUMMARY OF THE INVENTION

According to an aspect of the present invention, a radiation imaging control apparatus configured to control a radiation imaging operation using a radiation generation apparatus in which a radiation generation condition is adjustable by a manual operation includes a setting unit configured to set the radiation generation condition for the radiation imaging operation, a transmission unit configured to transmit the radiation generation condition to the radiation generation apparatus, and a transmission control unit configured to limit transmission of the radiation generation condition by the transmission unit in a case where a radiation imaging operation belonging to the same group as that of the radiation imaging operation is performed.

Further features of the present invention will become apparent from the following description of exemplary embodiments with reference to the attached drawings.

DESCRIPTION OF THE EMBODIMENTS

First Exemplary Embodiment

Figure 1:
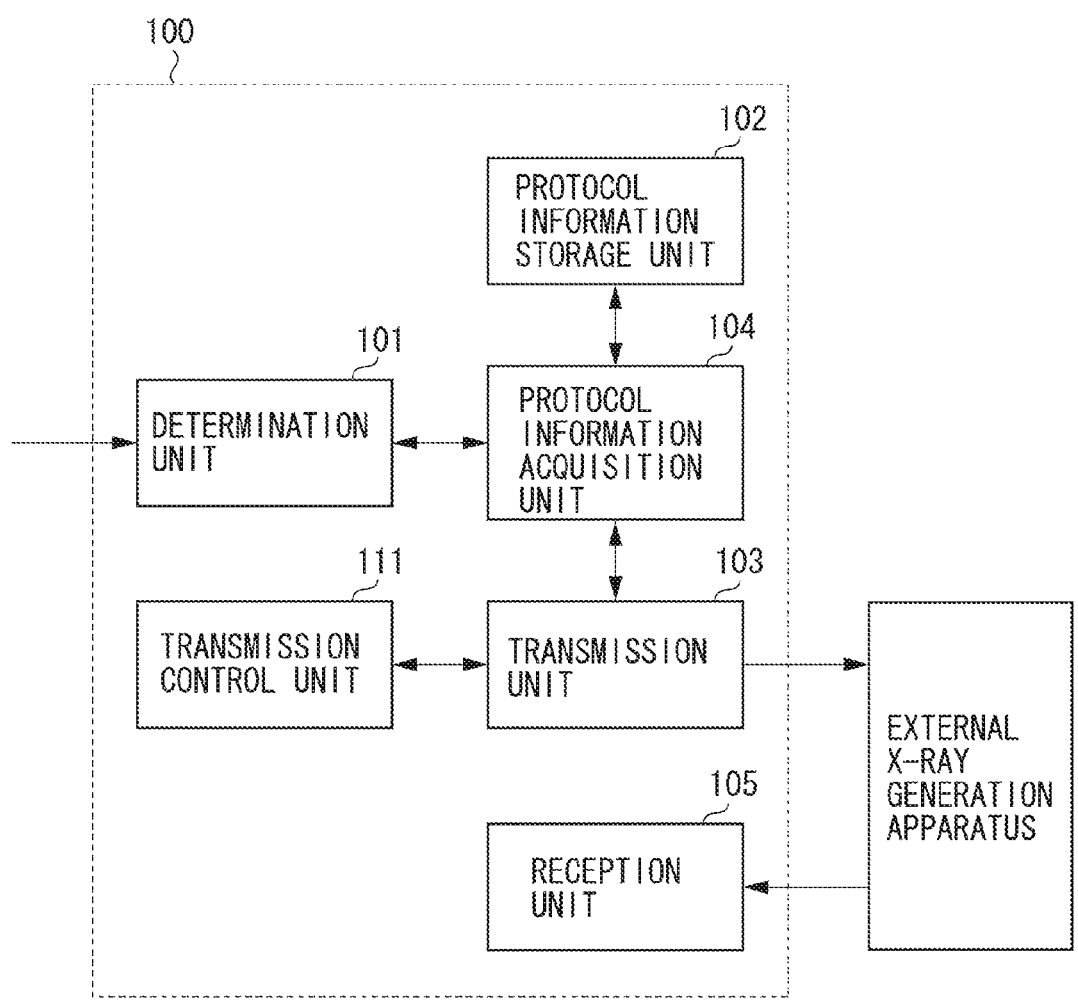
FIG. 1 is a block configuration diagram of first to fourth exemplary embodiments.

FIG. 1 is a block configuration diagram of an X-ray imaging control apparatus in a first exemplary embodiment, and illustrates a range 100 of the X-ray imaging control apparatus.

When an imaging protocol for an imaging object is selected previous to an X-ray imaging operation, a determination unit 101 determines the imaging protocol and communicates the imaging protocol to a protocol information acquisition unit 104.

A protocol information storage unit 102 stores protocol information corresponding to the imaging protocol. The protocol information acquisition unit 104 acquires the protocol information corresponding to the imaging protocol from the protocol information storage unit 102 using the imaging protocol communicated from the determination unit 101, and communicates the protocol information to a transmission unit 103.

The transmission unit 103 receives the protocol information from the protocol information acquisition unit 104, and receives a determination of whether the protocol information should be transmitted from a transmission control unit 111. When the transmission control unit 111 determines that the protocol information should be transmitted, the transmission unit 103 transmits the protocol information acquired from the protocol information acquisition unit 104 to an external X-ray generation apparatus. When the transmission control unit 111 determines that the protocol information should not be transmitted, the transmission unit 103 does not transmit the protocol information to the external X-ray generation apparatus.

When a radiation generation condition is changed by an operator's manual operation in the external X-ray generation apparatus, a reception unit 105 receives the changed protocol information from the external X-ray generation apparatus.

When the transmission control unit 111 receives the request of the determination of whether the protocol information should be transmitted from the transmission unit 103, and the imaging operation is a first imaging operation after the start of examination, the transmission control unit 111 communicates the determination of the transmission to the transmission unit 103. When the imaging operation is not the first imaging operation, the transmission control unit 111 communicates the determination of the non-transmission to the transmission unit 103.

The protocol information includes information required for an imaging operation as described below. Examples thereof include kV/mA/mAs/msec/diaphragm amount as X-ray generation parameters, number of times of completed imaging operations in examination, imaging target region information, target region direction information, imaging group information, update presence/absence information, phototimer position, relative position parameter, position linkage, and window width/window medium value/frequency emphatic parameter as image processing parameters.

Figure 2:
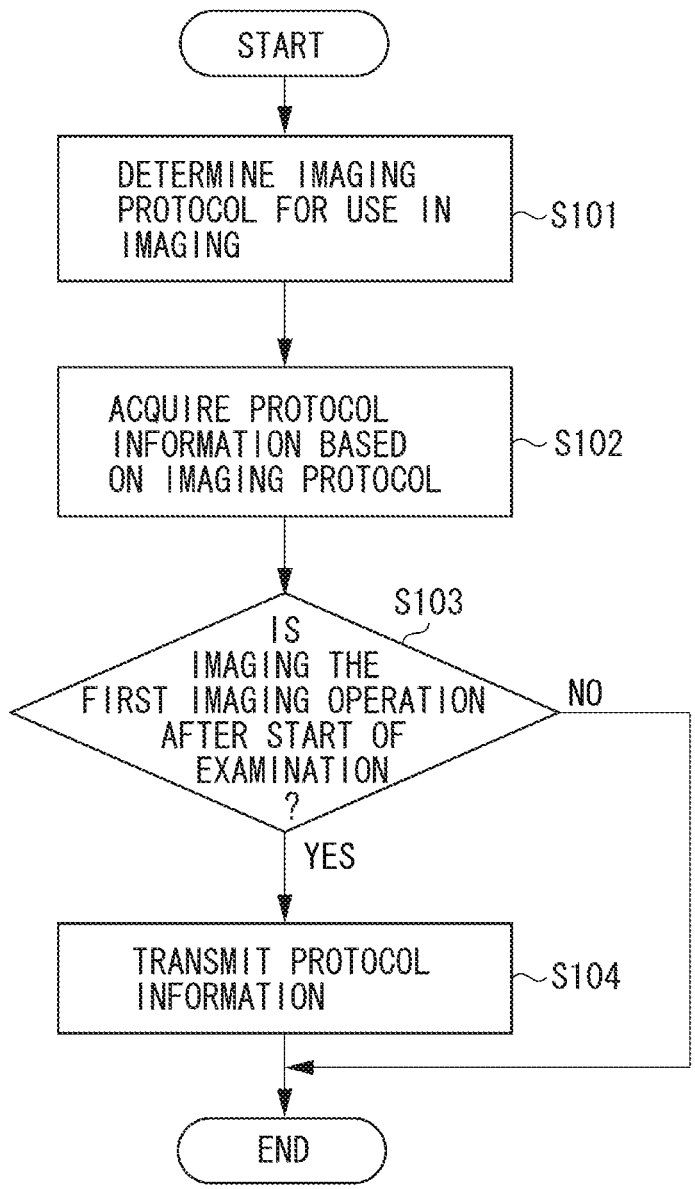
FIG. 2 is a flowchart of the first exemplary embodiment.

FIG. 2 is a flowchart of the X-ray imaging control apparatus in the first exemplary embodiment. FIG. 2 illustrates a process from the determination of the imaging protocol by the determination unit 101 in FIG. 1 to the transmission of the protocol information to the external X-ray generation apparatus by the transmission unit 103. In step S101, the determination unit 101 determines the imaging protocol for use in imaging, and communicates the imaging protocol to the protocol information acquisition unit 104.

In step S102, the protocol information acquisition unit 104 acquires the protocol information based on the imaging protocol from the protocol information storage unit 102 using the imaging protocol received in step S101, and communicates the acquired protocol information to the transmission unit 103.

In step S103, the transmission unit 103 receives the protocol information from the protocol information acquisition unit 104, and receives the determination of whether the protocol information should be transmitted from the transmission control unit 111. When the imaging operation is the first imaging operation after start of examination, the transmission control unit 111 communicates the determination of the transmission. When the imaging operation is not the first imaging operation after start of examination, the transmission control unit 111 communicates the determination of the non-transmission. When the transmission unit 103 receives the determination of the transmission from the transmission control unit 111, the transmission unit 103 transmits the protocol information communicated from the protocol information acquisition unit 104 in step S102 to the external X-ray generation apparatus in step S104, and ends the process. When the transmission unit 103 receives the determination of the non-transmission from the transmission control unit 111, the transmission unit 103 ends the process as it is without transmitting the protocol information to the external X-ray generation apparatus.

Second Exemplary Embodiment

A block configuration diagram in a second exemplary embodiment is the same as that of the first exemplary embodiment.

When the transmission control unit 111 receives the request of the determination of whether the protocol information should be transmitted from the transmission unit 103, and imaging group information in the protocol information and imaging group information in protocol information used for a previous imaging operation in the same examination do not belong to the same group, the transmission control unit 111 communicates the determination of the transmission to the transmission unit 103. When the two pieces of imaging group information belong to the same group, the transmission control unit 111 communicates the determination of the non-transmission to the transmission unit 103. The transmission control unit 111 retains the protocol information acquired from the transmission unit 103 until the next imaging operation in the same examination.

Figure 3:
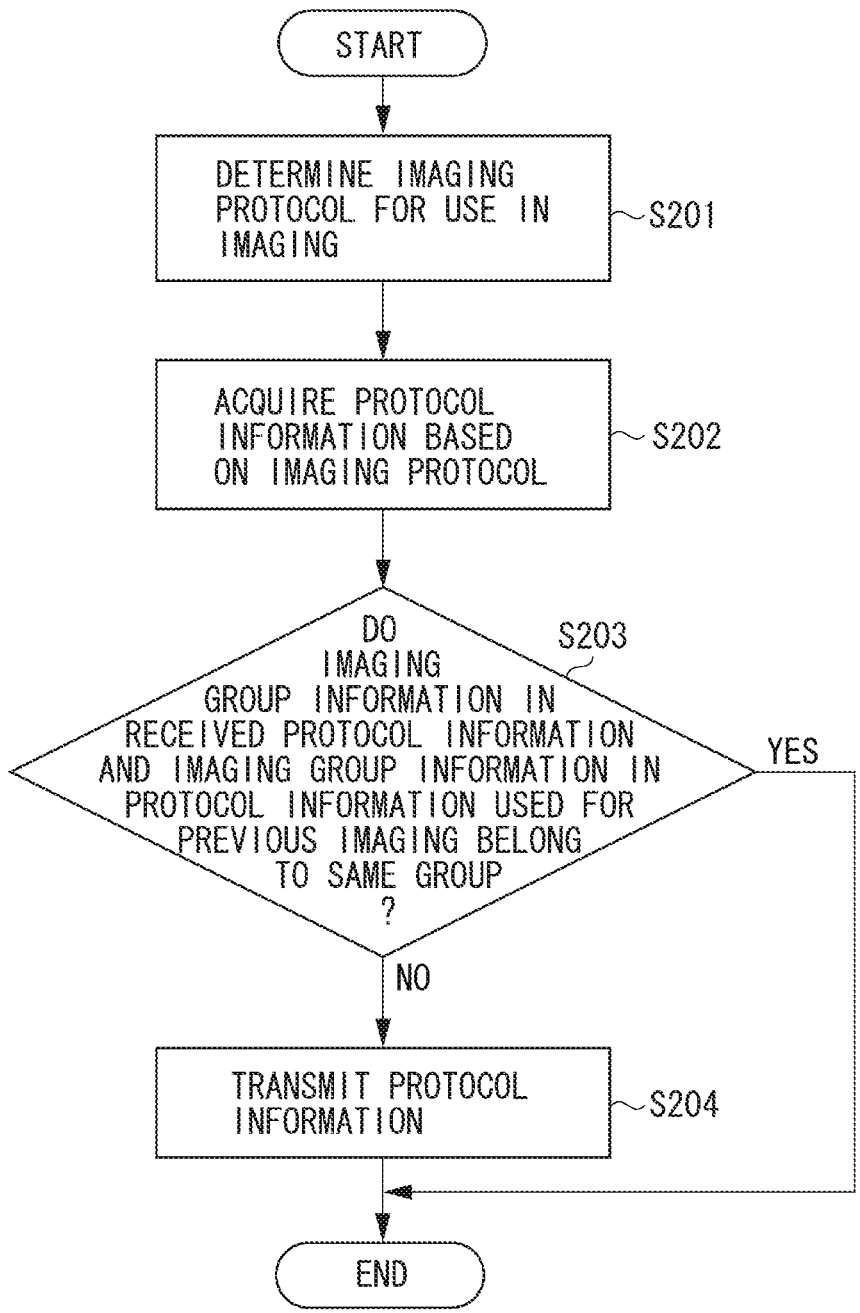
FIG. 3 is a flowchart of the second exemplary embodiment.

FIG. 3 is a flowchart of an X-ray imaging control apparatus in the second exemplary embodiment. FIG. 3 illustrates a process from the determination of the imaging protocol by the determination unit 101 in FIG. 1 to the transmission of the protocol information to the external X-ray generation apparatus by the transmission unit 103. In step S201, the determination unit 101 determines the imaging protocol for use in imaging, and communicates the imaging protocol to the protocol information acquisition unit 104.

In step S202, the protocol information acquisition unit 104 acquires the protocol information based on the imaging protocol from the protocol information storage unit 102 using the imaging protocol received in step S201, and communicates the acquired protocol information to the transmission unit 103.

Figure 4:
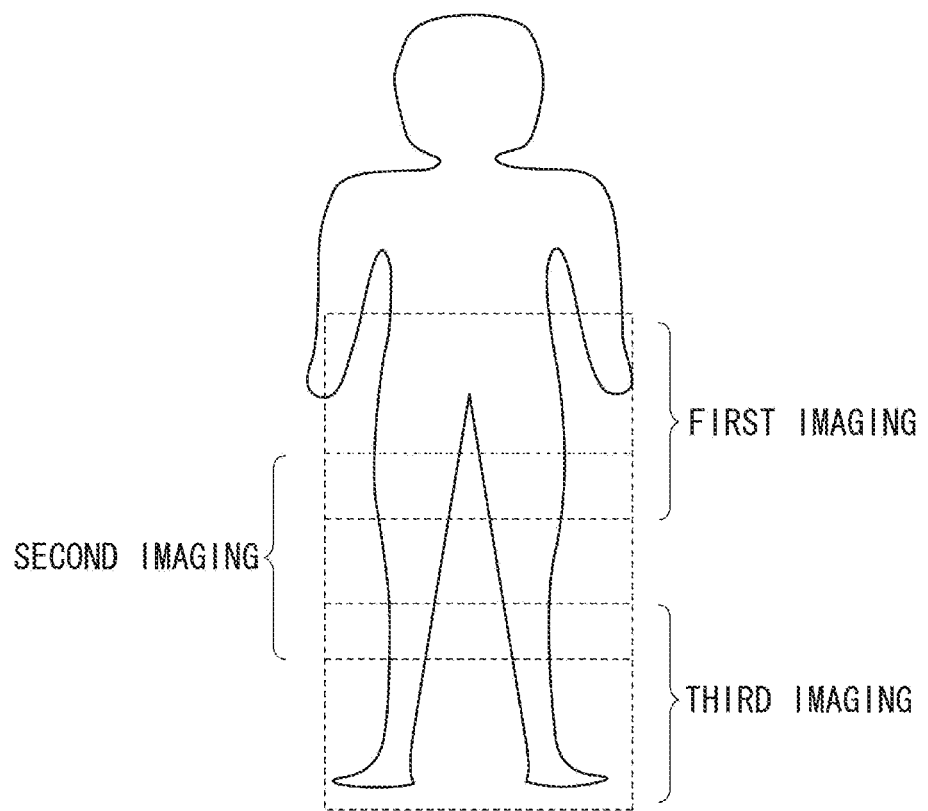
FIG. 4 illustrates a long-length imaging operation of the second exemplary embodiment.

In step S203, the transmission unit 103 receives the protocol information from the protocol information acquisition unit 104, and receives a determination of whether the protocol information should be transmitted from the transmission control unit 111. When the imaging group information in the protocol information received from the transmission unit 103 from the protocol information acquisition unit 104 and the imaging group information in protocol information used for a previous imaging operation in the same examination do not belong to the same group, the transmission control unit 111 communicates the determination of the transmission. When the two pieces of imaging group information belong to the same group, the transmission control unit 111 communicates the determination of the non-transmission. When the transmission unit 103 receives the determination of the transmission from the transmission control unit 111, the transmission unit 103 transmits the protocol information communicated from the protocol information acquisition unit 104 in step S202 to the external X-ray generation apparatus in step S204, and ends the process. When the transmission unit 103 receives the determination of the non-transmission from the transmission control unit 111, the transmission unit 103 ends the process as it is without transmitting the protocol information to the external X-ray generation apparatus. The same imaging group information in the present exemplary embodiment includes performing a plurality of imaging operations using one imaging protocol such as a long-length imaging operation. The long-length imaging operation means the following imaging technique. The whole length of a lower limb is imaged, for example, three times because an imaging area is insufficient in one imaging operation when the whole length of the lower limb is imaged as illustrated in FIG. 4, for example. Because the present exemplary embodiment determines the three imaging operations as the same imaging group information, the transmission unit 103 in FIG. 1 transmits the protocol information to the external X-ray generation apparatus for the first imaging operation, and the transmission unit 103 does not transmit the protocol information for the second and third imaging operations.

Third Exemplary Embodiment

A block configuration diagram in a third exemplary embodiment is the same as that of the first exemplary embodiment.

When the transmission control unit 111 receives the request of the determination of whether the protocol information should be transmitted from the transmission unit 103, and imaging target region information in the protocol information and imaging target region information in protocol information used for a previous imaging operation in the same examination do not belong to the same target region, the transmission control unit 111 communicates the determination of the transmission to the transmission unit 103. When the two pieces of imaging target region information belong to the same target region, the transmission control unit 111 communicates the determination of the non-transmission to the transmission unit 103. The transmission control unit 111 retains the protocol information acquired from the transmission unit 103 until the next imaging operation in the same examination.

Figure 5:
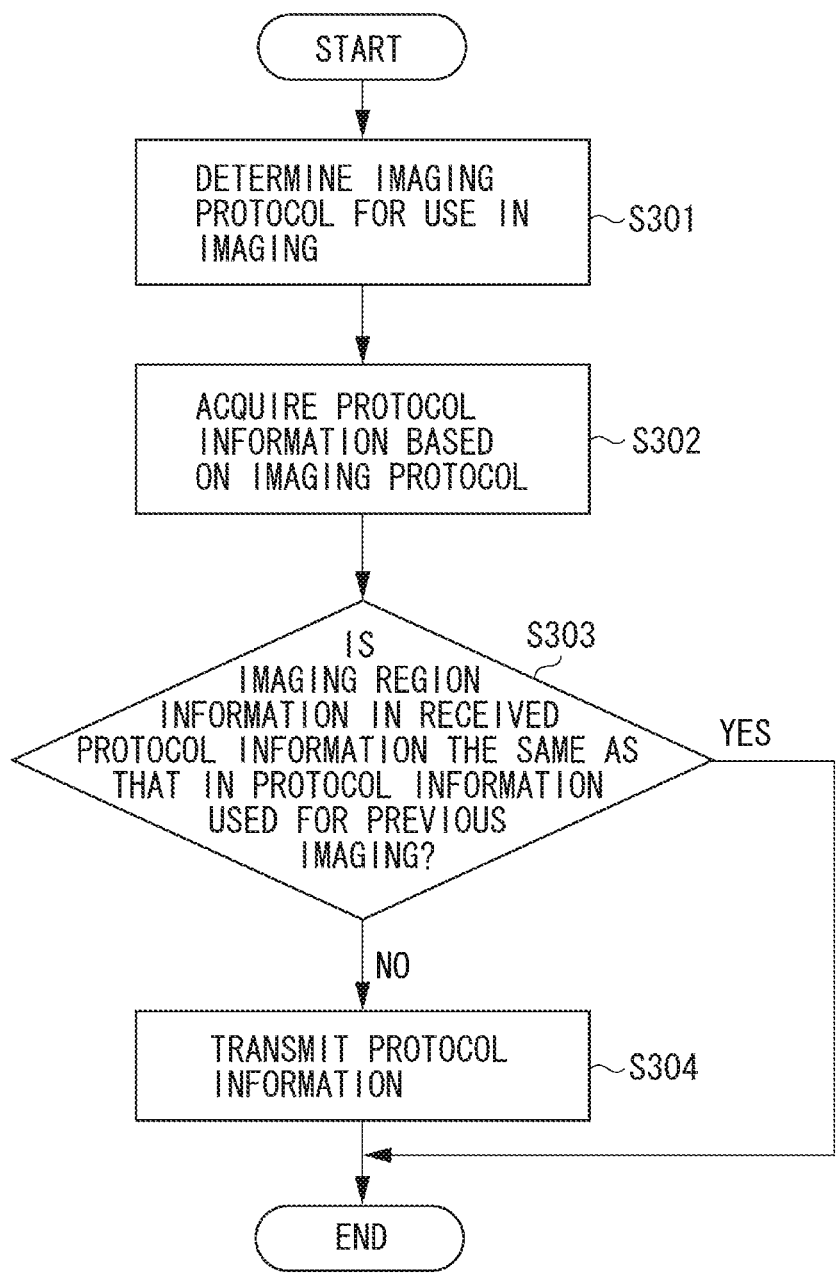
FIG. 5 is a flowchart of the third exemplary embodiment.

FIG. 5 is a flowchart of an X-ray imaging control apparatus in the third exemplary embodiment. FIG. 5 illustrates a process from the determination of the imaging protocol by the determination unit 101 in FIG. 1 to the transmission of the protocol information to the external X-ray generation apparatus by the transmission unit 103.

In step S301, the determination unit 101 determines the imaging protocol for use in imaging, and communicates the imaging protocol to the protocol information acquisition unit 104. In step S302, the protocol information acquisition unit 104 acquires the protocol information based on the imaging protocol from the protocol information storage unit 102 using the imaging protocol received in step S301, and communicates the acquired protocol information to the transmission unit 103. In step S303, the transmission unit 103 receives the protocol information from the protocol information acquisition unit 104, and receives a determination of whether the protocol information should be transmitted from the transmission control unit 111. When the imaging target region information in the protocol information received from the transmission unit 103 from the protocol information acquisition unit 104 and the imaging target region information in protocol information used for a previous imaging operation in the same examination do not belong to the same target region, the transmission control unit 111 communicates the determination of the transmission. When the two pieces of imaging target region information belong to the same target region, the transmission control unit 111 communicates the determination of the non-transmission. When the transmission unit 103 receives the determination of the transmission from the transmission control unit 111, the transmission unit 103 transmits the protocol information communicated from the protocol information acquisition unit 104 in step S302 to the external X-ray generation apparatus in step S304, and ends the process. When the transmission unit 103 receives the determination of the non-transmission from the transmission control unit 111, the transmission unit 103 ends the process as it is without transmitting the protocol information to the external X-ray generation apparatus.

The imaging target region information denotes an imaging object region such as a chest (CHEST) or an abdomen (ABDOMEN), for example. When the imaging target region information for the first imaging operation is CHEST, for example, and the imaging target region information for the second imaging operation is CHEST in the present exemplary embodiment, the transmission unit 103 does not transmit the protocol information in FIG. 1. When the imaging target region information for the first imaging operation is CHEST and the imaging target region information for the second imaging operation is ABDOMEN, for example, i.e., the two pieces of imaging target region information do not belong to the same target region, the transmission unit 103 transmits the protocol information to the external X-ray generation apparatus.

Fourth Exemplary Embodiment

A block configuration diagram in a fourth exemplary embodiment is the same as that of the first exemplary embodiment.

When the transmission control unit 111 receives the request of the determination of whether the protocol information should be transmitted from the transmission unit 103, and imaging target region information and target region direction information in the protocol information, and imaging target region information and target region direction information in protocol information used for a previous imaging operation in the same examination do not belong to the same target region and the same direction, the transmission control unit 111 communicates the determination of the transmission to the transmission unit 103. When the two pieces of imaging target region information and the two pieces of target region direction information belong to the same target region and the same direction, the transmission control unit 111 communicates the determination of the non-transmission to the transmission unit 103. The transmission control unit 111 retains the protocol information acquired from the transmission unit 103 until the next imaging operation in the same examination.

Figure 6:
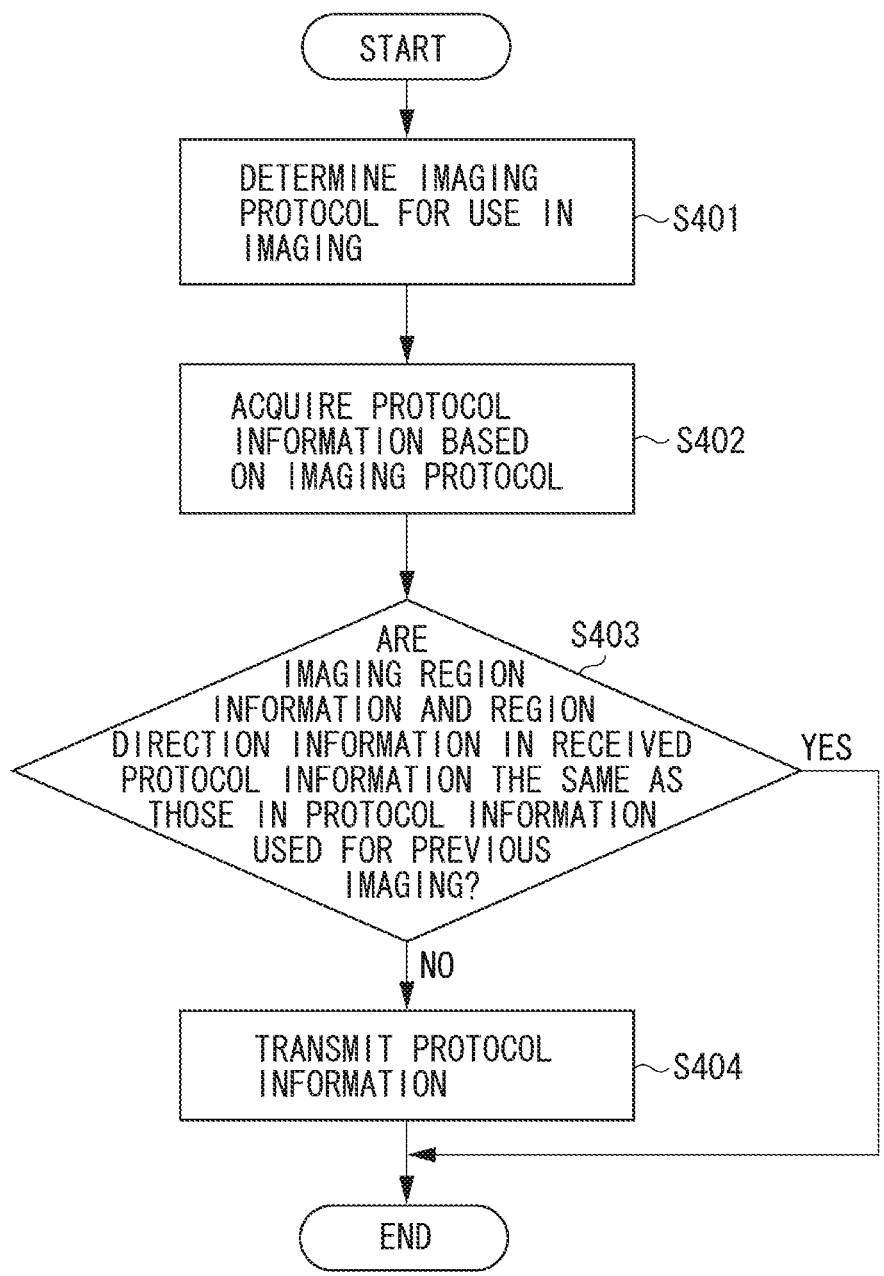
FIG. 6 is a flowchart of the fourth exemplary embodiment.

FIG. 6 is a flowchart of an X-ray imaging control apparatus in the fourth exemplary embodiment. FIG. 6 illustrates a process from the determination of the imaging protocol by the determination unit 101 in FIG. 1 to the transmission of the protocol information to the external X-ray generation apparatus by the transmission unit 103.

In step S401, the determination unit 101 determines the imaging protocol for use in imaging, and communicates the imaging protocol to the protocol information acquisition unit 104. In step S402, the protocol information acquisition unit 104 acquires the protocol information based on the imaging protocol from the protocol information storage unit 102 using the imaging protocol received in step S401, and communicates the acquired protocol information to the transmission unit 103. In step S403, the transmission unit 103 receives the protocol information from the protocol information acquisition unit 104, and receives a determination of whether the protocol information should be transmitted from the transmission control unit 111. When the imaging target region information and the target region direction information in the protocol information received from the transmission unit 103 from the protocol information acquisition unit 104, and the imaging target region information and the target region direction information in protocol information used for a previous imaging operation in the same examination do not belong to the same target region and the same direction, the transmission control unit 111 communicates the determination of the transmission. When the two pieces of imaging target region information and the two pieces of target region direction information belong to the same target region and the same direction, the transmission control unit 111 communicates the determination of the non-transmission. When the transmission unit 103 receives the determination of the transmission from the transmission control unit 111, the transmission unit 103 transmits the protocol information communicated from the protocol information acquisition unit 104 in step S402 to the external X-ray generation apparatus in step S404, and ends the process. When the transmission unit 103 receives the determination of the non-transmission from the transmission control unit 111, the transmission unit 103 ends the process as it is without transmitting the protocol information to the external X-ray generation apparatus.

The target region direction information denotes a direction for imaging an imaging object region such as Posterior to Anterior (PA) or Right to Left (RL), for example. When the imaging target region information and the target region direction information for the first imaging operation are CHEST/PA, for example, and the imaging target region information and the target region direction information for the second imaging operation are CHEST/PA in the present exemplary embodiment, the transmission unit 103 in FIG. 1 does not transmit the protocol information. When the imaging target region information for the second imaging operation is ABDOMEN/RL, CHEST/RL, or ABDOMEN/PA, for example, i.e., does not belong to the same target region and the same direction, the transmission unit 103 transmits the protocol information to the external X-ray generation apparatus.

Fifth Exemplary Embodiment

Figure 7:
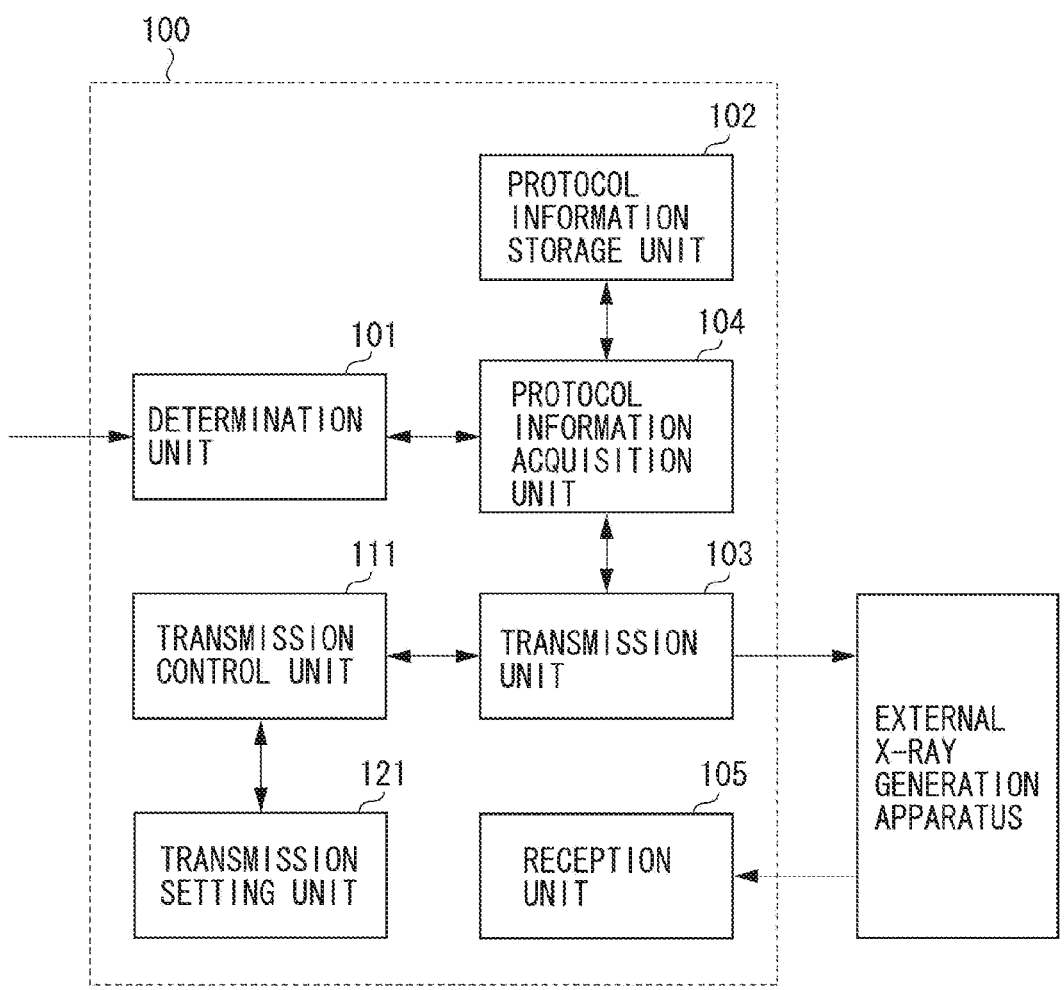
FIG. 7 is a block configuration diagram of a fifth exemplary embodiment.

FIG. 7 is a block configuration diagram of an X-ray imaging control apparatus in a fifth exemplary embodiment. The same blocks as those described in FIG. 1 are the same as those of the first exemplary embodiment.

A transmission setting unit 121 instructs the transmission control unit 111 to determine transmission in an optional state in examination to cause the transmission unit 103 to compulsorily transmit protocol information to the external X-ray generation apparatus.

For example, when a condition where the transmission control unit 111 communicates the determination of the non-transmission to the transmission unit 103 is fulfilled in the second exemplary embodiment, the transmission setting unit 121 instructs the transmission control unit 111 to determine transmission to cause the transmission unit 103 to compulsorily transmit the protocol information even when the transmission unit 103 does not transmit the protocol information to the external X-ray generation apparatus.

Sixth Exemplary Embodiment

Figure 8:
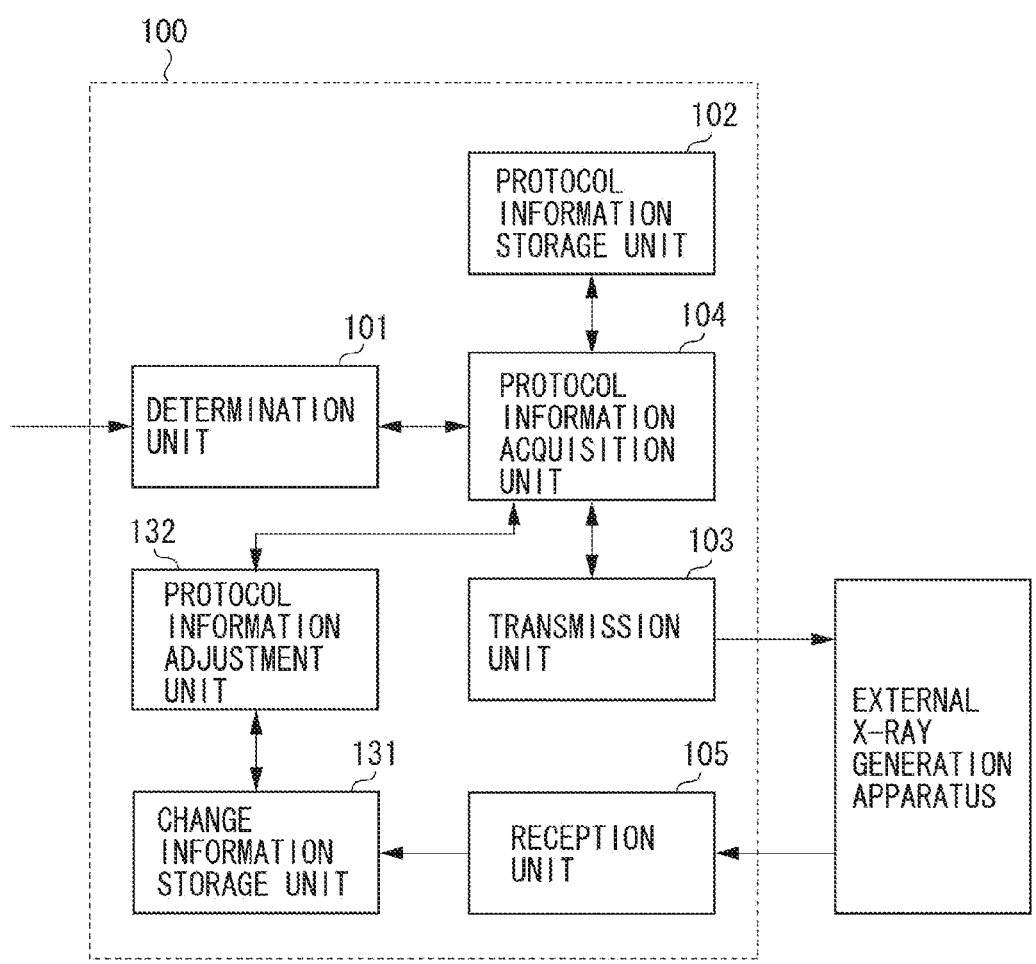
FIG. 8 is a block configuration diagram of sixth and seventh exemplary embodiments.

FIG. 8 is a block configuration diagram of an X-ray imaging control apparatus in a sixth exemplary embodiment, and illustrates a range 100 of the X-ray imaging control apparatus.

When the imaging protocol as the imaging object is selected previous to the X-ray imaging operation, the determination unit 101 determines the imaging protocol, and communicates the determined imaging protocol to the protocol information acquisition unit 104.

The protocol information storage unit 102 stores protocol information corresponding to the imaging protocol. The protocol information acquisition unit 104 acquires the protocol information corresponding to the imaging protocol from the protocol information storage unit 102 using the imaging protocol communicated from the determination unit 101. The protocol information acquisition unit 104 acquires protocol information adjusted to a suitable content by a protocol information adjustment unit 132 using the acquired protocol information, and communicates the adjusted protocol information to the transmission unit 103.

The protocol information acquisition unit 104 communicates the protocol information to the transmission unit 103. The transmission unit 103 transmits the communicated protocol information to the external X-ray generation apparatus.

When an operator changes the protocol information in the external X-ray generation apparatus, the reception unit 105 receives the changed protocol information, and communicates the protocol information to a change information storage unit 131.

The change information storage unit 131 stores the protocol information communicated by the reception unit 105.

The protocol information adjustment unit 132 acquires a difference between an initial value of protocol information used for a previous imaging operation and the protocol information changed for the previous imaging operation stored in the change information storage unit 131. Furthermore, the protocol information adjustment unit 132 adjusts the protocol information received from the protocol information acquisition unit 104 using the acquired difference, and communicates the adjusted protocol information to the protocol information acquisition unit 104. The protocol information adjustment unit 132 retains the initial value of the protocol information acquired from the protocol information acquisition unit 104 until the next imaging operation in the same examination.

Figure 9:
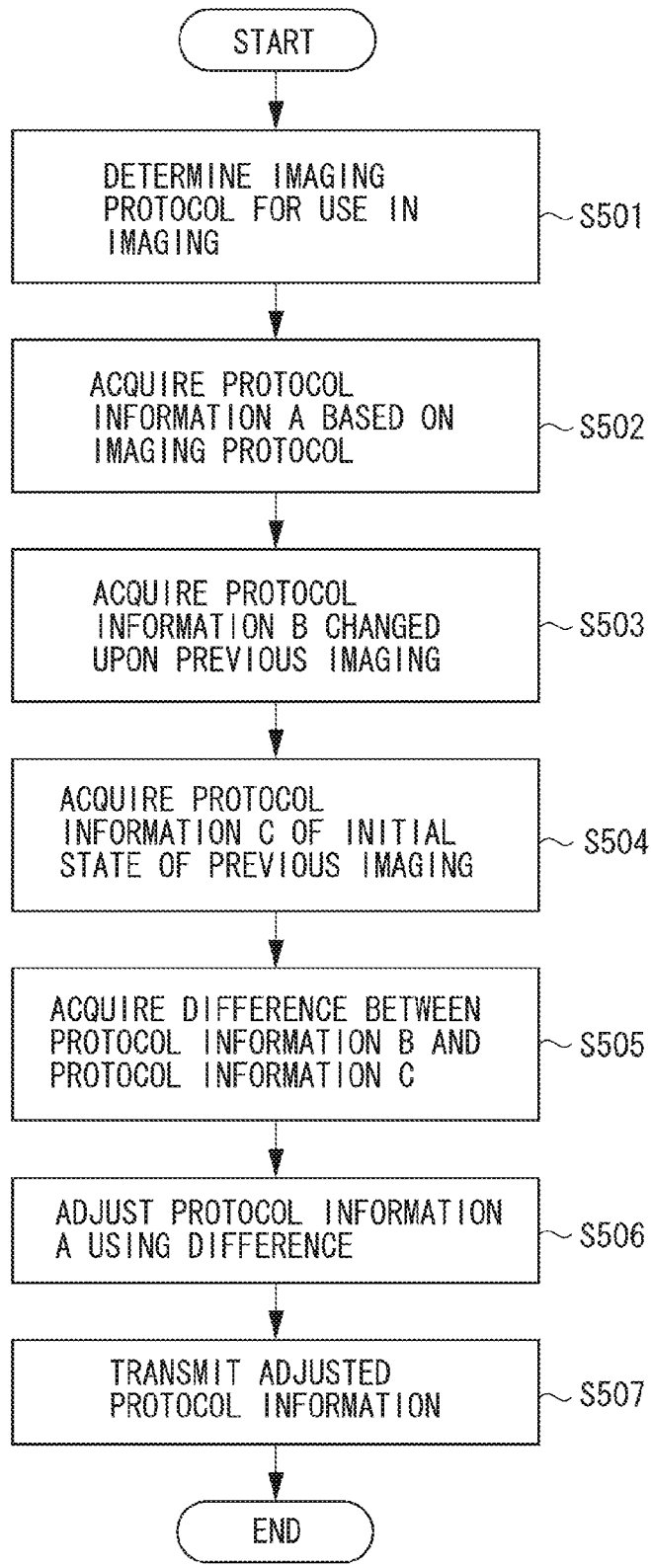
FIG. 9 is a flowchart of the sixth exemplary embodiment.

FIG. 9 is a flowchart of the X-ray imaging control apparatus in the sixth exemplary embodiment. FIG. 9 illustrates a process from the determination of the imaging protocol by the determination unit 101 in FIG. 8 to the transmission of the protocol information to the external X-ray generation apparatus by the transmission unit 103.

In step S501, the determination unit 101 determines the imaging protocol for use in imaging, and communicates the imaging protocol to the protocol information acquisition unit 104. In step S502, the protocol information acquisition unit 104 acquires the protocol information based on the imaging protocol from the protocol information storage unit 102 using the imaging protocol received in step S501, and communicates the acquired protocol information to the protocol information adjustment unit 132. The protocol information is defined as protocol information A. In step S503, the protocol information adjustment unit 132 acquires the protocol information changed for the previous imaging operation from the change information storage unit 131. The protocol information is defined as protocol information B. In step S504, the protocol information adjustment unit 132 acquires the initial value of the protocol information communicated from the protocol information acquisition unit 104 for the previous imaging operation and retained by the protocol information adjustment unit 132.

The protocol information is defined as protocol information C. In step S505, the protocol information adjustment unit 132 acquires a difference between the protocol information B and the protocol information C. In step S506, the protocol information adjustment unit 132 adjusts the protocol information A using the acquired difference, and communicates the adjusted protocol information A to the protocol information acquisition unit 104. The protocol information acquisition unit 104 communicates the communicated protocol information A to the transmission unit 103. In step S507, the transmission unit 103 transmits the adjusted protocol information A to the external X-ray generation apparatus, and ends the process.

Seventh Exemplary Embodiment

A block configuration diagram in a seventh exemplary embodiment is the same as that of the sixth exemplary embodiment.

The protocol information adjustment unit 132 acquires a ratio between an initial value of protocol information used for a previous imaging operation and the protocol information changed for the previous imaging operation stored in the change information storage unit 131. Furthermore, the protocol information adjustment unit 132 adjusts the protocol information received from the protocol information acquisition unit 104 using the acquired ratio, and communicates the adjusted protocol information to the protocol information acquisition unit 104. The protocol information adjustment unit 132 retains the initial value of the protocol information acquired from the protocol information acquisition unit 104 until the next imaging operation in the same examination.

Figure 10:
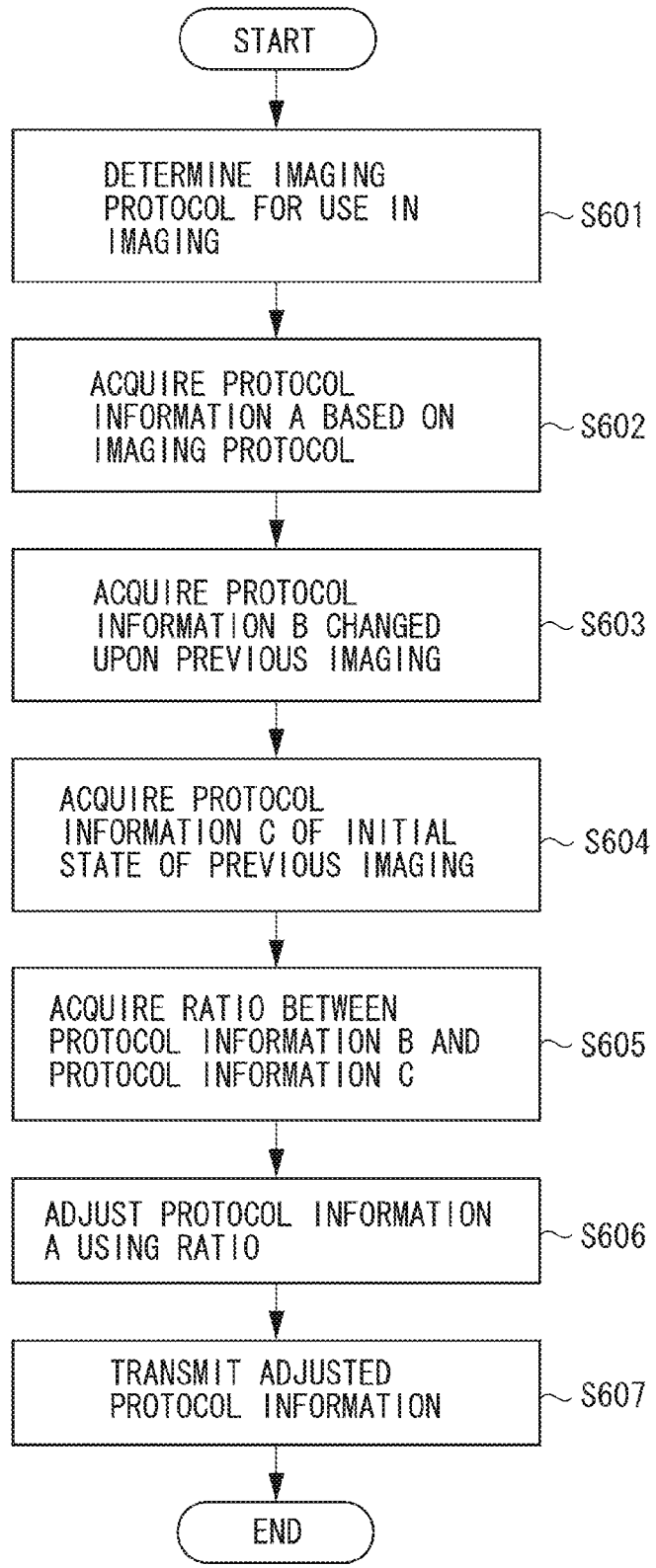
FIG. 10 is a flowchart of the seventh exemplary embodiment.

FIG. 10 is a flowchart of an X-ray imaging control apparatus in the seventh exemplary embodiment. FIG. 10 illustrates a process from the determination of the imaging protocol by the determination unit 101 in FIG. 8 to the transmission of the protocol information to the external X-ray generation apparatus by the transmission unit 103.

In step S601, the determination unit 101 determines the imaging protocol for use in imaging, and transmits the imaging protocol to the protocol information acquisition unit 104. In step S602, the protocol information acquisition unit 104 acquires the protocol information based on the imaging protocol from the protocol information storage unit 102 using the imaging protocol received in step S601, and communicates the acquired protocol information to the protocol information adjustment unit 132. The protocol information is defined as protocol information A. In step S603, the protocol information adjustment unit 132 acquires the protocol information changed for the previous imaging operation from the change information storage unit 131. The protocol information is defined as protocol information B. In step S604, the protocol information adjustment unit 132 acquires the initial value of the protocol information communicated from the protocol information acquisition unit 104 for the previous imaging operation and retained by the protocol information adjustment unit 132.

The protocol information is defined as protocol information C. In step S605, the protocol information adjustment unit 132 acquires a ratio between the protocol information B and the protocol information C.

In step S606, the protocol information adjustment unit 132 adjusts the protocol information A using the acquired ratio, and communicates the adjusted protocol information A to the protocol information acquisition unit 104. The protocol information acquisition unit 104 communicates the communicated protocol information A to the transmission unit 103. In step S607, the transmission unit 103 transmits the adjusted protocol information A to the external X-ray generation apparatus, and ends the process.

Eighth Exemplary Embodiment

Figure 11:
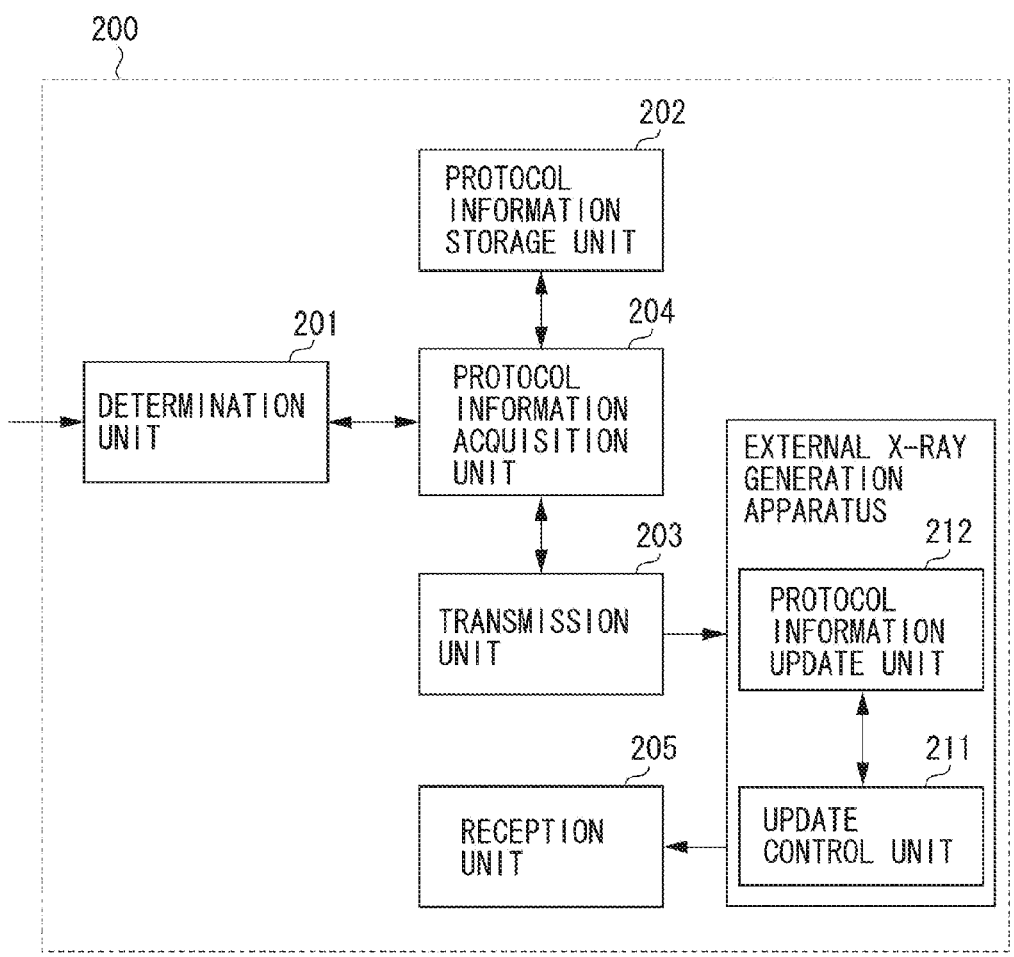
FIG. 11 is a block configuration diagram of eighth to 11th and 15th exemplary embodiments.

FIG. 11 is a block configuration diagram of an X-ray image collection system in an eighth exemplary embodiment, and illustrates a range 200 of the X-ray image collection system.

When an imaging protocol for an imaging object is selected previous to an X-ray imaging operation, a determination unit 201 determines the imaging protocol, and communicates the determined imaging protocol to a protocol information acquisition unit 204.

A protocol information storage unit 202 stores protocol information corresponding to the imaging protocol.

The protocol information acquisition unit 204 acquires the protocol information corresponding to the imaging protocol from the protocol information storage unit 202 using the imaging protocol communicated from the determination unit 201. The protocol information acquisition unit 204 communicates the acquired protocol information to a transmission unit 203.

The transmission unit 203 receives the protocol information from the protocol information acquisition unit 204, and transmits the protocol information to an external X-ray generation apparatus.

When an operator changes the protocol information in the external X-ray generation apparatus, a reception unit 205 receives the changed protocol information.

A protocol information update unit 212 receives the protocol information from the transmission unit 203, and receives a determination of whether the protocol information should be updated from an update control unit 211. When the update control unit 211 determines that the protocol information should be updated, the protocol information update unit 212 updates the protocol information of the external X-ray generation apparatus using the protocol information received from the transmission unit 203. When the update control unit 211 determines that the protocol information should not be updated, the protocol information update unit 212 does not update the protocol information of the external X-ray generation apparatus.

When the update control unit 211 receives the request of the determination of whether the protocol information should be transmitted from the protocol information update unit 212, and when the imaging operation is a first imaging operation after the start of examination, the update control unit 211 communicates the determination of the update to the protocol information update unit 212. When the imaging operation is not the first imaging operation, the update control unit 211 communicates the determination of the non-update to the protocol information update unit 212.

Figure 12:
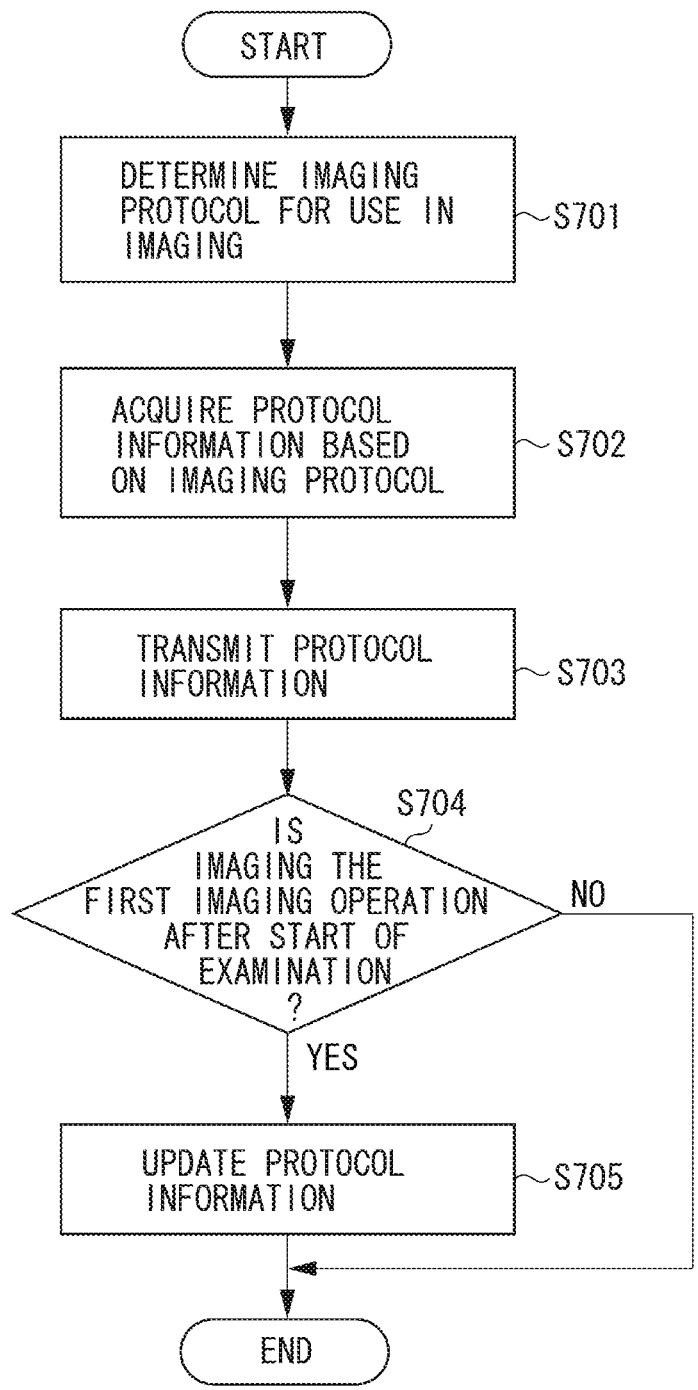
FIG. 12 is a flowchart of the eighth exemplary embodiment.

FIG. 12 is a flowchart of the X-ray image collection system in the eighth exemplary embodiment. FIG. 12 illustrates a process from the determination of the imaging protocol by the determination unit 201 in FIG. 11 to the update of the protocol information of the external X-ray generation apparatus by the protocol information update unit 212.

In step S701, the determination unit 201 determines the imaging protocol, and communicates the imaging protocol to the protocol information acquisition unit 204. In step S702, the protocol information acquisition unit 204 acquires the protocol information based on the imaging protocol from the protocol information storage unit 202 using the imaging protocol received in step S701, and communicates the acquired protocol information to the transmission unit 203. In step S703, the transmission unit 203 transmits the protocol information received in step S702 to the external X-ray generation apparatus.

In step S704, the protocol information update unit 212 receives the protocol information received from the transmission unit 203, and receives a determination of whether the protocol information should be updated from the update control unit 211. When the imaging operation is the first imaging operation after start of examination, the update control unit 211 communicates the determination of the update to the protocol information update unit 212. When the imaging operation is not the first imaging operation, the update control unit 211 communicates the determination of the non-update to the protocol information update unit 212. When the protocol information update unit 212 receives the determination of the update from the update control unit 211, the protocol information update unit 212 updates the protocol information of the external X-ray generation apparatus in step S705, and ends the process. When the protocol information update unit 212 receives the determination of the non-update from the update control unit 211, the protocol information update unit 212 ends the process as it is without updating the protocol information of the external X-ray generation apparatus.

Ninth Exemplary Embodiment

A block configuration diagram in a ninth exemplary embodiment is the same as that of the eighth exemplary embodiment.

When the update control unit 211 receives the request of the determination of whether the protocol information should be updated from the protocol information update unit 212, and when imaging group information in the protocol information and imaging group information in protocol information used for a previous imaging operation do not belong to the same group, the update control unit 211 communicates the determination of the update to the protocol information update unit 212. When the two pieces of imaging group information belong to the same group, the update control unit 211 communicates the determination of the non-update to the protocol information update unit 212. The update control unit 211 retains the protocol information acquired from the protocol information update unit 212 until the next imaging operation in the same examination.

Figure 13:
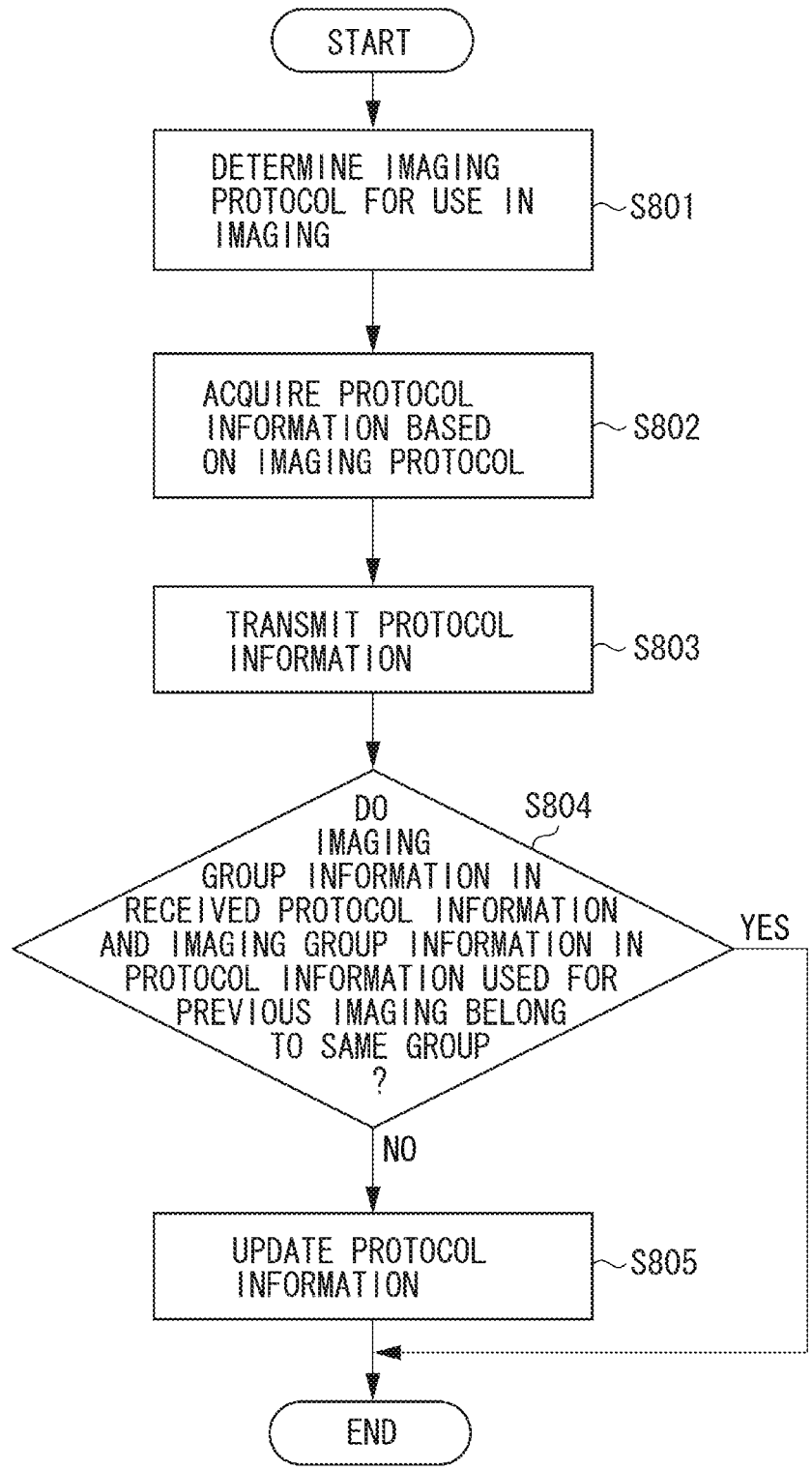
FIG. 13 is a flowchart of the ninth exemplary embodiment.

FIG. 13 is a flowchart of an X-ray image collection system in the ninth exemplary embodiment. FIG. 13 illustrates a process from the determination of the imaging protocol by the determination unit 201 in FIG. 11 to the update of the protocol information of the external X-ray generation apparatus by the protocol information update unit 212.

In step S801, the determination unit 201 determines the imaging protocol, and communicates the imaging protocol to the protocol information acquisition unit 204. In step S802, the protocol information acquisition unit 204 acquires the protocol information based on the imaging protocol from the protocol information storage unit 202 using the imaging protocol received in step S801, and communicates the acquired protocol information to the transmission unit 203.

In step S803, the transmission unit 203 transmits the protocol information received in step S802 to the external X-ray generation apparatus.

In step S804, the protocol information update unit 212 receives a determination of whether the protocol information should be updated from the update control unit 211 using the protocol information received from the transmission unit 203. When imaging group information in the received protocol information and imaging group information in protocol information used for a previous imaging operation in the same examination do not belong to the same group, the update control unit 211 communicates the determination of the update to the protocol information update unit 212. When the two pieces of imaging group information belong to the same group, the update control unit 211 communicates the determination of the non-update to the protocol information update unit 212. When the protocol information update unit 212 receives the determination of the update from the update control unit 211, the protocol information update unit 212 updates the protocol information of the external X-ray generation apparatus in step S805, and ends the process. When the protocol information update unit 212 receives the determination of the non-update from the update control unit 211, the protocol information update unit 212 ends the process as it is without updating the protocol information of the external X-ray generation apparatus.

10th Exemplary Embodiment

A block configuration diagram in a 10th exemplary embodiment is the same as that of the eighth exemplary embodiment.

When the update control unit 211 receives the request of the determination of whether the protocol information should be updated from the protocol information update unit 212, and when imaging target region information in the protocol information and imaging target region information in protocol information used for a previous imaging operation do not belong to the same target region, the update control unit 211 communicates the determination of the update to the protocol information update unit 212. When the two pieces of imaging target region information belong to the same target region, the update control unit 211 communicates the determination of the non-update to the protocol information update unit 212. The update control unit 211 retains the protocol information acquired from the protocol information update unit 212 until the next imaging operation in the same examination.

Figure 14:
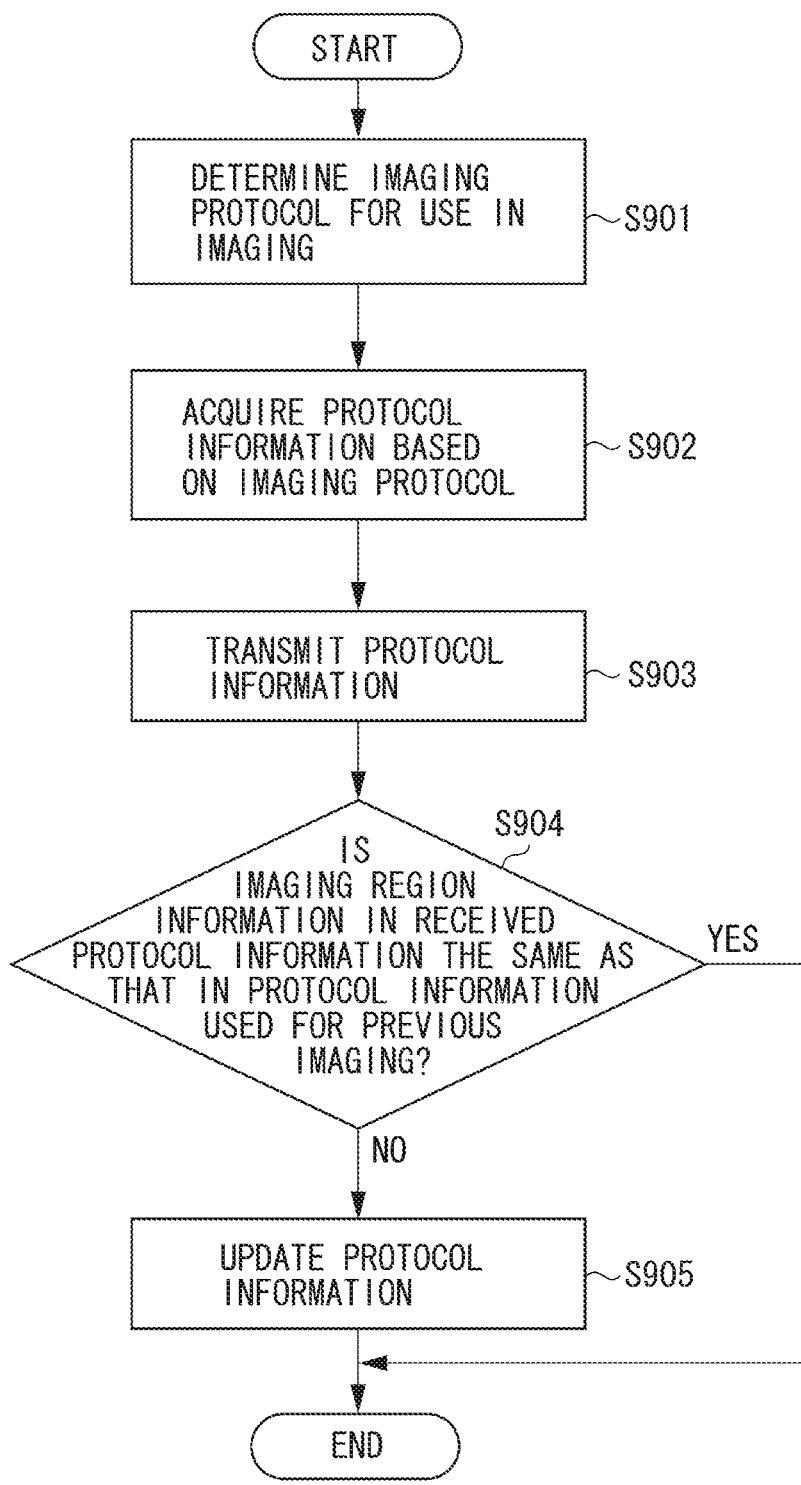
FIG. 14 is a flowchart of the 10th exemplary embodiment.

FIG. 14 is a flowchart of an X-ray image collection system in the 10th exemplary embodiment. FIG. 14 illustrates a process from the determination of the imaging protocol by the determination unit 201 in FIG. 11 to the update of the protocol information of the external X-ray generation apparatus by the protocol information update unit 212.

In step S901, the determination unit 201 determines the imaging protocol, and communicates the imaging protocol to the protocol information acquisition unit 204. In step S902, the protocol information acquisition unit 204 acquires the protocol information based on the imaging protocol from the protocol information storage unit 202 using the imaging protocol received in step S901, and communicates the acquired protocol information to the transmission unit 203. In step S903, the transmission unit 203 transmits the protocol information received in step S902 to the external X-ray generation apparatus.

In step S904, the protocol information update unit 212 receives a determination of whether the protocol information should be updated from the update control unit 211 using the protocol information received from the transmission unit 203. When imaging target region information in the received protocol information and imaging target region information in protocol information used for a previous imaging operation in the same examination do not belong to the same target region, the update control unit 211 communicates the determination of the update to the protocol information update unit 212. When the two pieces of imaging target region information belong to the same target region, the update control unit 211 communicates the determination of the non-update to the protocol information update unit 212. When the protocol information update unit 212 receives the determination of the update from the update control unit 211, the protocol information update unit 212 updates the protocol information of the external X-ray generation apparatus in step S905, and ends the process. When the protocol information update unit 212 receives the determination of the non-update from the update control unit 211, the protocol information update unit 212 ends the process as it is without updating the protocol information of the external X-ray generation apparatus.

11th Exemplary Embodiment

A block configuration diagram in an 11th exemplary embodiment is the same as that of the eighth exemplary embodiment. When the update control unit 211 receives the request of the determination of whether the protocol information should be updated from the protocol information update unit 212, and imaging target region information and target region direction information in the protocol information, and imaging target region information and target region direction information in protocol information used for a previous imaging operation do not belong to the same target region and the same direction, the update control unit 211 communicates the determination of the update to the protocol information update unit 212. When the two pieces of imaging target region information and the two pieces of target region direction information belong to the same target region and the same direction, the update control unit 211 communicates the determination of the non-update to the protocol information update unit 212. The update control unit 211 retains the protocol information acquired from the protocol information update unit 212 until the next imaging operation in the same examination.

Figure 15:
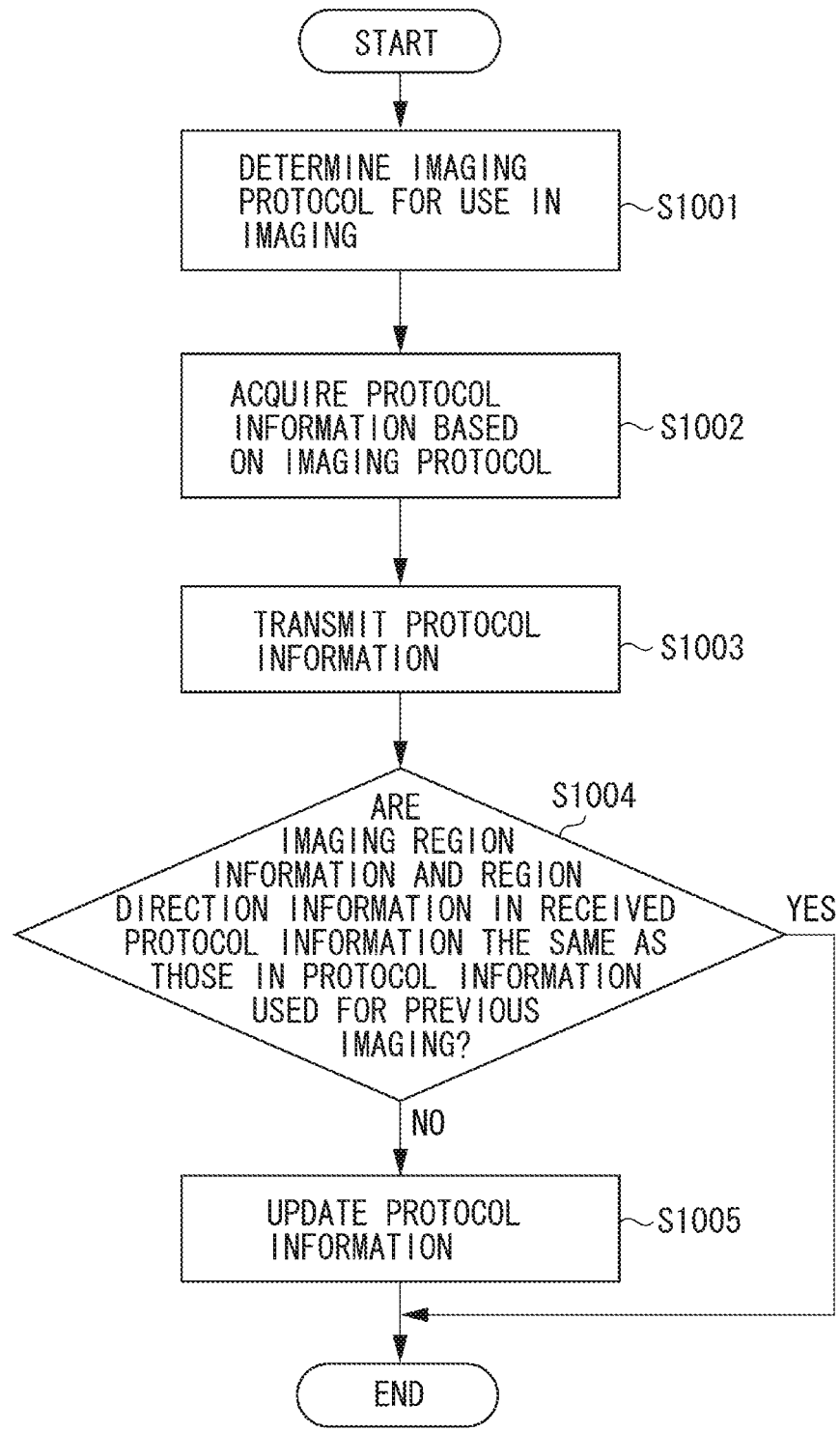
FIG. 15 is a flowchart of the 11th exemplary embodiment.

FIG. 15 is a flowchart of an X-ray image collection system in the 11th exemplary embodiment. FIG. 15 illustrates a process from the determination of the imaging protocol by the determination unit 201 in FIG. 11 to the update of the protocol information of the external X-ray generation apparatus by the protocol information update unit 212.

In step S1001, the determination unit 201 determines the imaging protocol, and communicates the imaging protocol to the protocol information acquisition unit 204. In step S1002, the protocol information acquisition unit 204 acquires the protocol information based on the imaging protocol from the protocol information storage unit 202 using the imaging protocol received in step S1001, and communicates the acquired protocol information to the transmission unit 203.

In step S1003, the transmission unit 203 transmits the protocol information received in step S1002 to the external X-ray generation apparatus.

In step S1004, the protocol information update unit 212 receives a determination of whether the protocol information should be updated from the update control unit 211 using the protocol information received from the transmission unit 203. When imaging target region information and target region direction information in the received protocol information, and imaging target region information and target region direction information in protocol information used for a previous imaging operation in the same examination do not belong to the same target region and the same direction, the update control unit 211 communicates the determination of the update to the protocol information update unit 212. When the two pieces of imaging target region information and the two pieces of target region direction information belong to the same target region and the same direction, the update control unit 211 communicates the determination of the non-update to the protocol information update unit 212. When the protocol information update unit 212 receives the determination of the update from the update control unit 211, the protocol information update unit 212 updates the protocol information of the external X-ray generation apparatus in step S1005, and ends the process. When the protocol information update unit 212 receives the determination of the non-update from the update control unit 211, the protocol information update unit 212 ends the process as it is without updating the protocol information of the external X-ray generation apparatus.

12th Exemplary Embodiment

Figure 16:
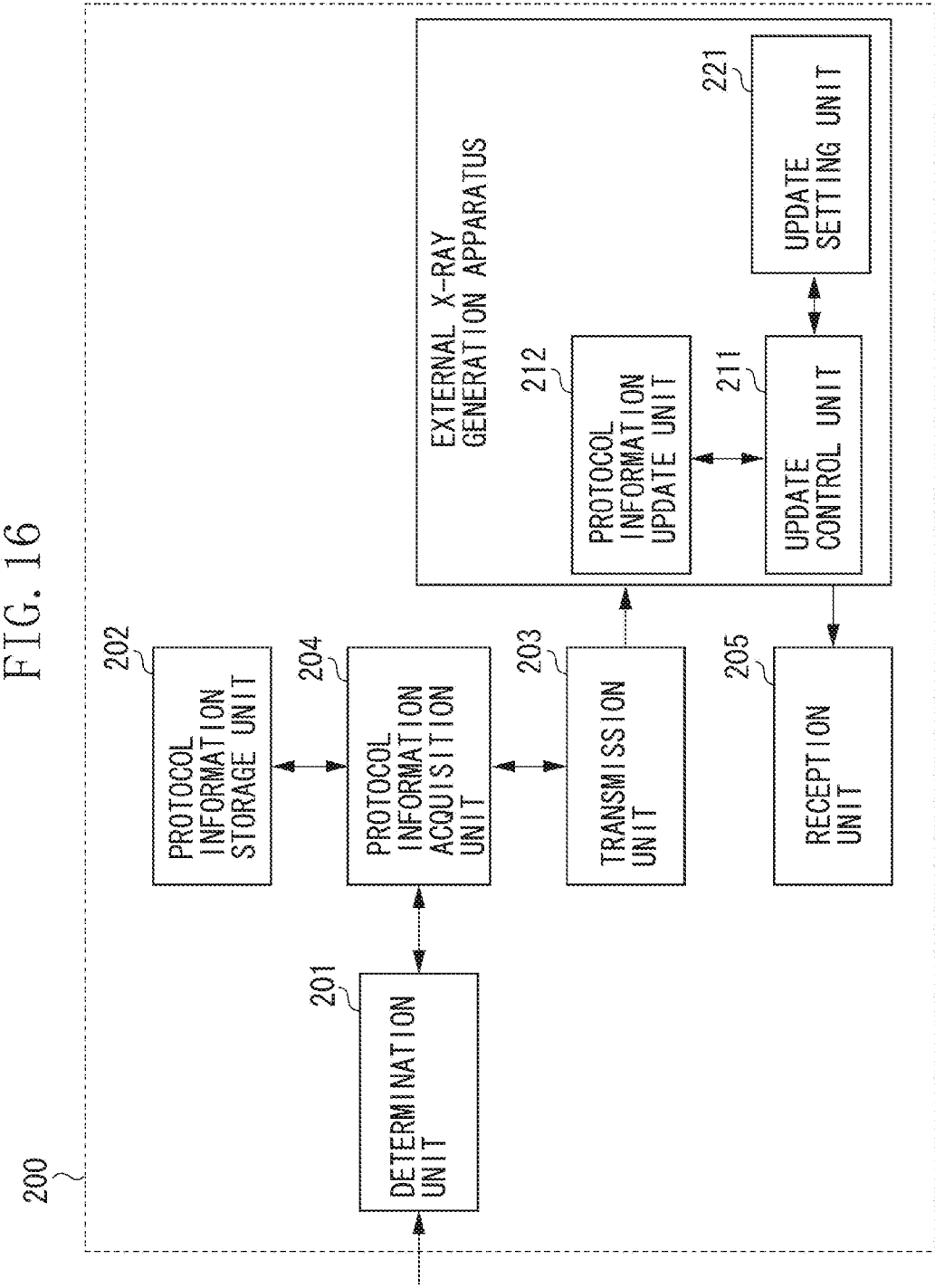
FIG. 16 is a block configuration diagram of a 12th exemplary embodiment.

FIG. 16 is a block configuration diagram of an X-ray image collection system in a 12th exemplary embodiment. The same blocks as those described in FIG. 11 are the same as those of the eighth exemplary embodiment.

An update setting unit 221 instructs the update control unit 211 to determine update in an optional state to cause the protocol information update unit 212 to compulsorily update the protocol information of the external X-ray generation apparatus.

For example, when a condition where the update control unit 211 communicates the determination of the non-update to the protocol information update unit 212 is fulfilled in the ninth exemplary embodiment, the update setting unit 221 instructs the update control unit 211 to determine update to cause the transmission unit 103 to compulsorily update the protocol information even when the protocol information update unit 212 does not update the protocol information of the external X-ray generation apparatus.

13th Exemplary Embodiment

Figure 17:
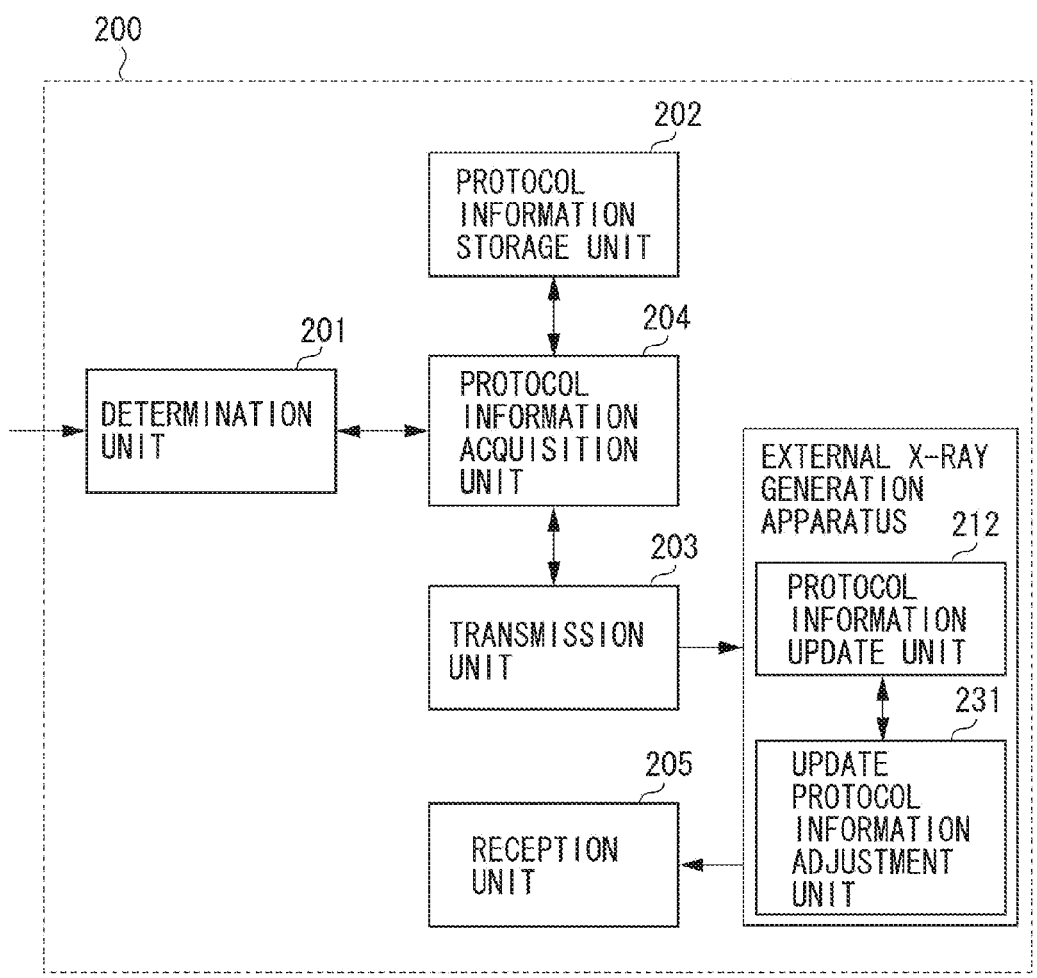
FIG. 17 is a block configuration diagram of 13th and 14th exemplary embodiments.

FIG. 17 is a block configuration diagram of an X-ray image collection system in a 13th exemplary embodiment, and illustrates a range 200 of the X-ray image collection system. When an imaging protocol for an imaging object is selected previous to an X-ray imaging operation, a determination unit 201 determines the imaging protocol, and communicates the determined imaging protocol to a protocol information acquisition unit 204.

A protocol information storage unit 202 stores protocol information corresponding to the imaging protocol.

The protocol information acquisition unit 204 acquires the protocol information corresponding to the imaging protocol from the protocol information storage unit 202 using the imaging protocol communicated from the determination unit 201, and communicates the acquired protocol information to a transmission unit 203.

The transmission unit 203 receives the protocol information from the protocol information acquisition unit 204, and transmits the protocol information to an external X-ray generation apparatus.

When an operator changes the protocol information in the external X-ray generation apparatus, a reception unit 205 receives the changed protocol information.

A protocol information update unit 212 acquires protocol information adjusted to a suitable content by an update protocol information adjustment unit 231 using the protocol information received from the transmission unit 203, and updates the protocol information of the external X-ray generation apparatus.

The update protocol information adjustment unit 231 acquires a difference between an initial value of protocol information used for a previous imaging operation and protocol information actually used for the previous imaging operation. Furthermore, the update protocol information adjustment unit 231 adjusts the protocol information received from the protocol information update unit 212 using the acquired difference, and communicates the adjusted protocol information to the protocol information update unit 212. The update protocol information adjustment unit 231 retains the initial value of the protocol information acquired from the protocol information update unit 212 until the next imaging operation in the same examination.

Figure 18:
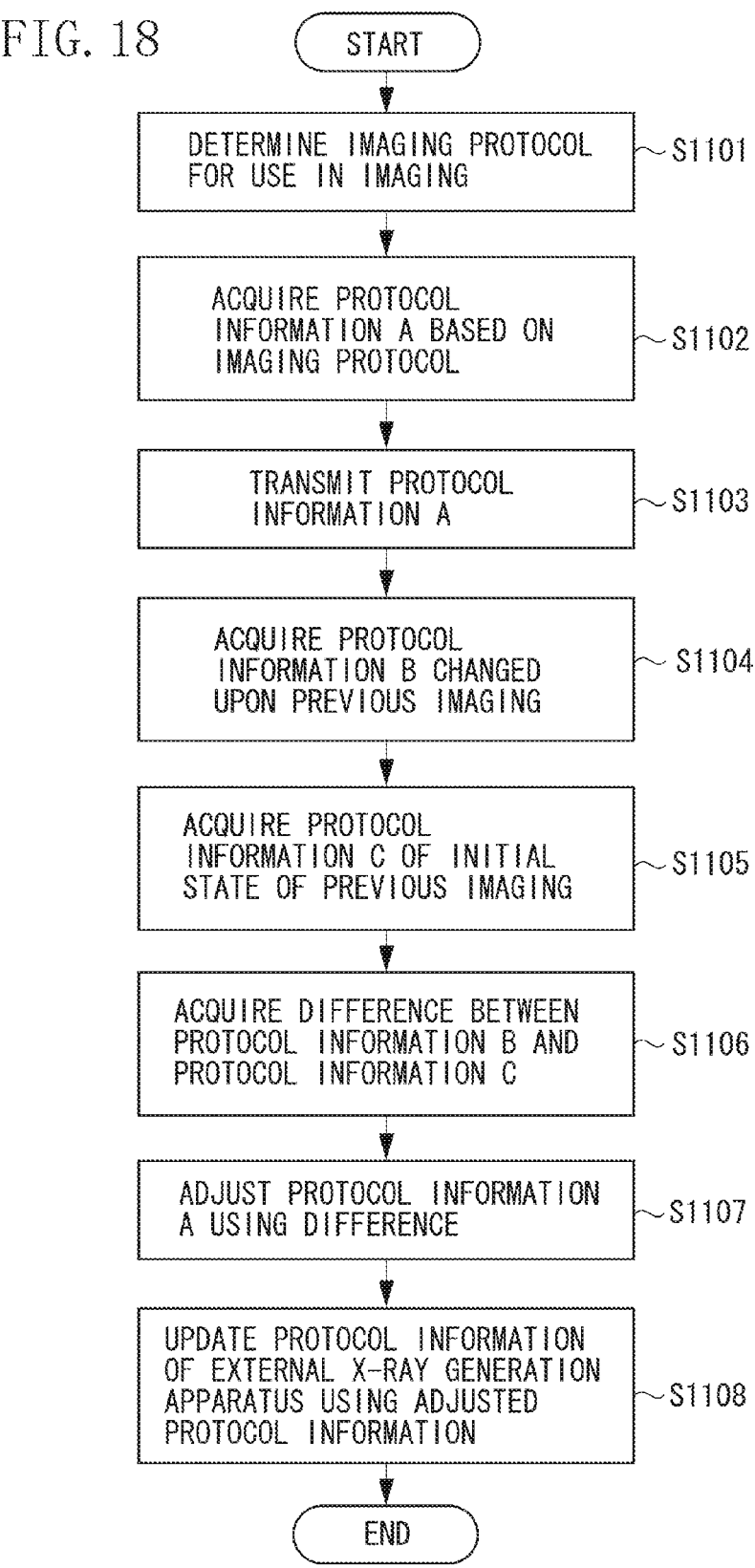
FIG. 18 is a flowchart of the 13th exemplary embodiment.

FIG. 18 is a flowchart of an X-ray image collection system in the 13th exemplary embodiment. FIG. 18 illustrates a process from the determination of the imaging protocol by the determination unit 201 in FIG. 17 to the update of the protocol information of the external X-ray generation apparatus by the protocol information update unit 212.

In step S1101, the determination unit 201 determines the imaging protocol for use in imaging, and communicates the imaging protocol to the protocol information acquisition unit 204. In step S1102, the protocol information acquisition unit 204 acquires the protocol information based on the imaging protocol from the protocol information storage unit 202 using the imaging protocol received in step S1101, and communicates the acquired protocol information to the transmission unit 203. The protocol information is defined as protocol information A.

In step S1103, the transmission unit 203 transmits the protocol information A to the external X-ray generation apparatus.

In step S1104, the protocol information update unit 212 communicates the protocol information A received by the external X-ray generation apparatus to the update protocol information adjustment unit 231. The update protocol information adjustment unit 231 acquires protocol information used for a previous imaging operation from the external X-ray generation apparatus. The protocol information is defined as protocol information B.

In step S1105, the update protocol information adjustment unit 231 acquires the initial value of the protocol information communicated from the protocol information update unit 212 for the previous imaging operation and retained by the update protocol information adjustment unit 231. The protocol information is defined as protocol information C.

In step S1106, the update protocol information adjustment unit 231 acquires a difference between the protocol information B and the protocol information C.

In step S1107, the update protocol information adjustment unit 231 adjusts the protocol information A using the acquired difference, and communicates the adjusted protocol information A to the protocol information update unit 212.

In step S1108, the protocol information update unit 212 updates the protocol information of the external X-ray generation apparatus using the adjusted protocol information A, and ends the process.

14th Exemplary Embodiment

A block configuration diagram in a 14th exemplary embodiment is the same as that of the 13th exemplary embodiment.

The update protocol information adjustment unit 231 acquires a ratio between an initial value of protocol information used for a previous imaging operation and protocol information actually used for the previous imaging operation. Furthermore, the update protocol information adjustment unit 231 adjusts the protocol information received from the protocol information update unit 212 using the acquired ratio, and communicates the adjusted protocol information to the protocol information update unit 212. The update protocol information adjustment unit 231 retains the initial value of the protocol information acquired from the protocol information update unit 212 until the next imaging operation in the same examination.

Figure 19:
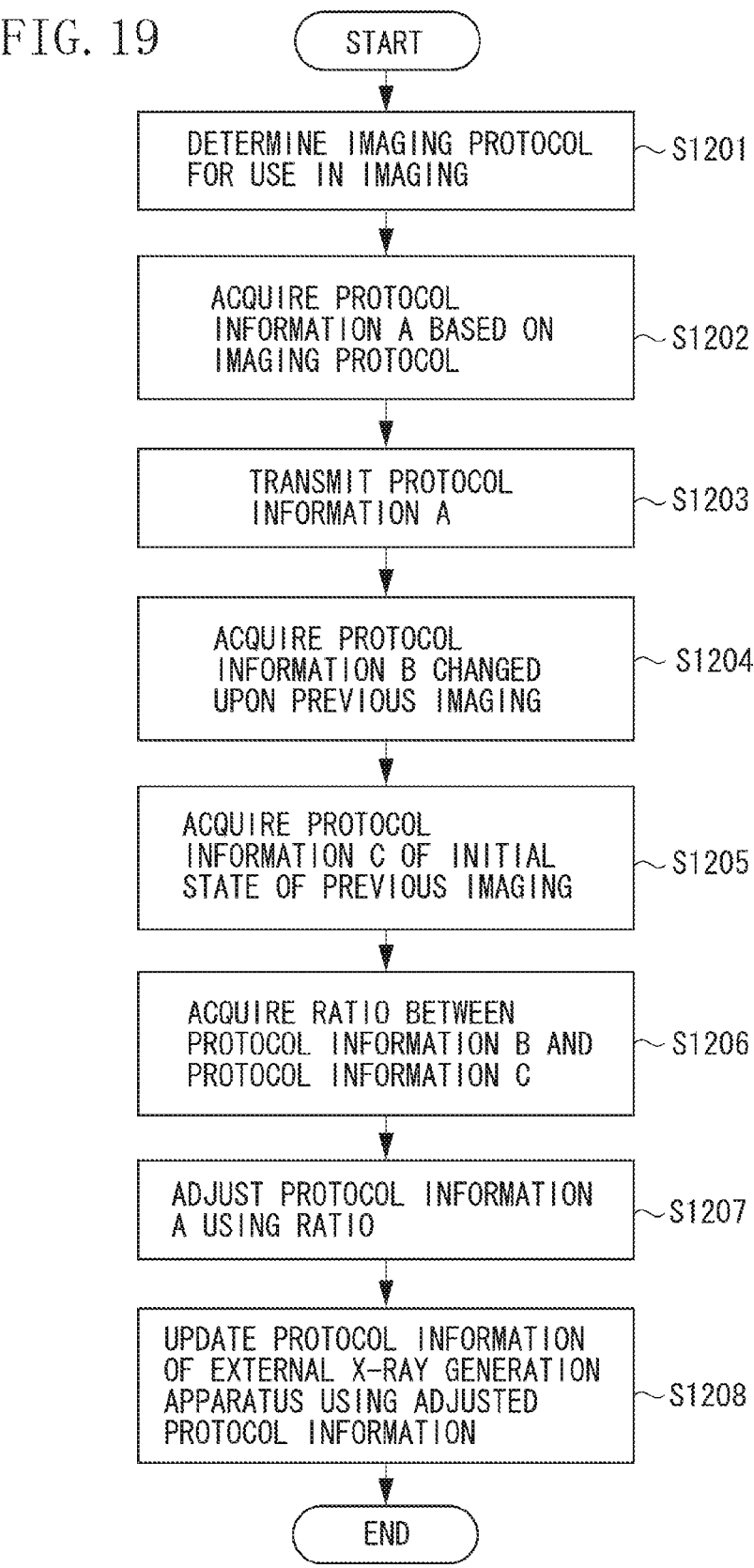
FIG. 19 is a flowchart of the 14th exemplary embodiment.

FIG. 19 is a flowchart of an X-ray image collection system in the 14th exemplary embodiment. FIG. 19 illustrates a process from the determination of the imaging protocol by the determination unit 201 in FIG. 17 to the update of the protocol information of the external X-ray generation apparatus by the protocol information update unit 212.

In step S1201, the determination unit 201 determines the imaging protocol for use in imaging, and communicates the imaging protocol to the protocol information acquisition unit 204. In step S1202, the protocol information acquisition unit 204 acquires the protocol information based on the imaging protocol from the protocol information storage unit 202 using the imaging protocol received in step S1201, and communicates the acquired protocol information to the transmission unit 203. The protocol information is defined as protocol information A.

In step S1203, the transmission unit 203 transmits the protocol information A to the external X-ray generation apparatus.

In step S1204, the protocol information update unit 212 communicates the protocol information A received by the external X-ray generation apparatus to the update protocol information adjustment unit 231. The update protocol information adjustment unit 231 acquires the protocol information changed by an operator for the previous imaging operation and retained by the update protocol information adjustment unit 231. The protocol information is defined as protocol information B.

In step S1205, the update protocol information adjustment unit 231 acquires the initial value of the protocol information communicated from the protocol information update unit 212 for the previous imaging operation and retained by the update protocol information adjustment unit 231. The protocol information is defined as protocol information C.

In step S1206, the update protocol information adjustment unit 231 acquires a ratio between the protocol information B and the protocol information C.

In step S1207, the update protocol information adjustment unit 231 adjusts the protocol information A using the acquired ratio, and communicates the adjusted protocol information A to the protocol information update unit 212.

In step S1208, the protocol information update unit 212 updates the protocol information of the external X-ray generation apparatus using the adjusted protocol information A, and ends the process.

15th Exemplary Embodiment

A block configuration diagram in a 15th exemplary embodiment is the same as that of the eighth exemplary embodiment.

The update control unit 211 communicates the determination of update to the protocol information update unit 212 based on update presence/absence information added to protocol information when the update presence/absence information indicates presence. When the update presence/absence information indicates absence, the update control unit 211 communicates the determination of non-update to the protocol information update unit 212.

Figure 20:
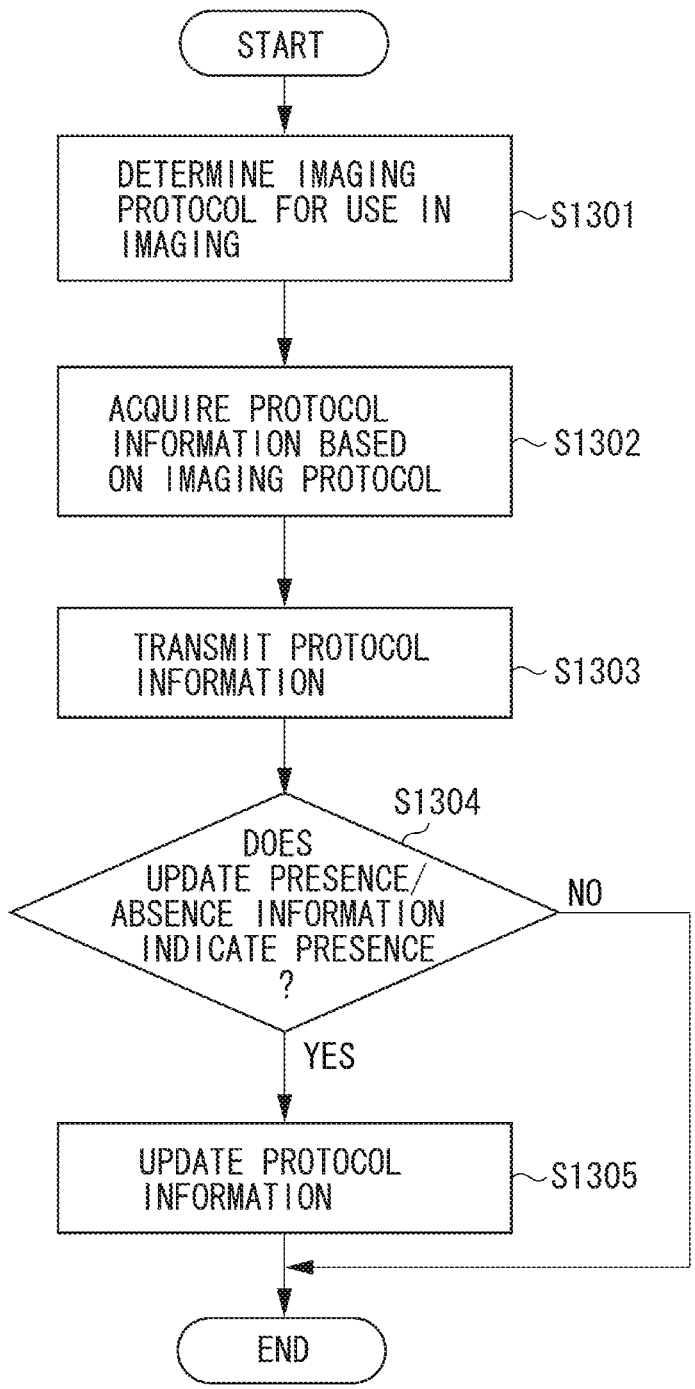
FIG. 20 is a flowchart of the 15th exemplary embodiment.

FIG. 20 is a flowchart of an X-ray image collection system in the 15th exemplary embodiment. FIG. 20 illustrates a process from the determination of the imaging protocol by the determination unit 201 in FIG. 11 to the update of the protocol information of the external X-ray generation apparatus by the protocol information update unit 212.

In step S1301, the determination unit 201 determines the imaging protocol, and communicates the imaging protocol to the protocol information acquisition unit 204. In step S1302, the protocol information acquisition unit 204 acquires the protocol information based on the imaging protocol from the protocol information storage unit 202 using the imaging protocol received in step S1301, and communicates the acquired protocol information to the transmission unit 203.

In step S1303, the transmission unit 203 transmits the protocol information received in step S1302 to the external X-ray generation apparatus.

In step S1304, the protocol information update unit 212 receives a determination of whether the protocol information should be updated from the update control unit 211 using the protocol information received from the transmission unit 203. When the update presence/absence information in the received protocol information indicates presence, the update control unit 211 communicates the determination of the update to the protocol information update unit 212. When the update presence/absence information indicates absence, the update control unit 211 communicates the determination of the non-update to the protocol information update unit 212. When the protocol information update unit 212 receives the determination of the update from the update control unit 211, the protocol information update unit 212 updates the protocol information of the external X-ray generation apparatus in step S1305, and ends the process. When the protocol information update unit 212 receives the determination of the non-update from the update control unit 211, the protocol information update unit 212 ends the process as it is without updating the protocol information of the external X-ray generation apparatus.

When the operator updates the protocol information on an external input unit in the external X-ray generation apparatus in the present exemplary embodiment, the operator's update is effective even when the protocol information update unit 212 receives the determination of the non-update from the update control unit 211. The X-ray imaging control flows performed in the exemplary embodiments may be read by a computer program recorded in a computer-readable recording medium, and may be conducted by a computer configured to function as the radiation imaging control apparatus.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment (s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-135829 filed Jun. 15, 2012, which is hereby incorporated by reference herein in its entirety.

What is claimed is:

1. A radiation imaging control apparatus configured to control a radiation imaging operation using a radiation generation apparatus in which a radiation generation condition is adjustable by a manual operation, the radiation imaging control apparatus comprising:
a setting unit configured to set the radiation generation condition for the radiation imaging operation;
a transmission unit configured to transmit the radiation generation condition to the radiation generation apparatus; and
a transmission control unit configured to limit transmission of the radiation generation condition by the transmission unit in a case where a radiation imaging operation belonging to the same group as that of the radiation imaging operation is performed.

2. The radiation imaging control apparatus according to claim 1, wherein the same group is a long-length imaging group in which a plurality of imaging operations are performed under one radiation generation condition.

3. The radiation imaging control apparatus according to claim 1, wherein the transmission control unit limits the transmission of the radiation generation condition in a case where an imaging operation is performed based on a second radiation generation condition after an imaging operation based on a first radiation generation condition, and in a case where an imaging target region of the imaging operation based on the first radiation generation condition is the same as an imaging target region of the imaging operation based on the second radiation generation condition.

4. The radiation imaging control apparatus according to claim 1, wherein the transmission control unit limits the transmission of the radiation generation condition in a case where an imaging operation is performed based on a second radiation generation condition after an imaging operation based on a first radiation generation condition, and in a case where an imaging target region and target region direction of the imaging operation based on the first radiation generation condition are the same as those of the imaging operation based on the second radiation generation condition.

5. The radiation imaging control apparatus according to claim 1, further comprising a transmission setting unit configured to cause the transmission unit to transmit the radiation generation condition based on a user instruction in a case where the transmission of the radiation generation condition is limited by the transmission control unit.

6. A radiation imaging control apparatus configured to control a radiation imaging operation using a radiation generation apparatus in which a radiation generation condition is adjustable by a manual operation, the radiation imaging control apparatus comprising:
a setting unit configured to set the radiation generation condition for the radiation imaging operation;
a transmission unit configured to transmit the radiation generation condition to the radiation generation apparatus; and
a transmission control unit configured to cause the transmission unit to transmit a second radiation generation condition based on a difference between a first radiation generation condition adjusted by the manual operation and the first radiation generation condition before being adjusted by the manual operation in a case where an imaging operation based on the second radiation generation condition is performed after an imaging operation based on the first radiation generation condition adjusted by the manual operation.

7. The radiation imaging control apparatus according to claim 6, wherein the transmission control unit is configured to cause the transmission unit to transmit the second radiation generation condition based on a ratio between the first radiation generation condition adjusted by the manual operation and the first radiation generation condition before being adjusted by the manual operation in a case where the imaging operation based on the second radiation generation condition is performed after the imaging operation based on the first radiation generation condition adjusted by the manual operation.

8. A method for controlling a radiation imaging control apparatus configured to control a radiation imaging operation using a radiation generation apparatus in which a radiation generation condition is adjustable by a manual operation, the method comprising:
    setting the radiation generation condition for the radiation imaging operation;
    transmitting the radiation generation condition to the radiation generation apparatus; and
    limiting transmission of the radiation generation condition in a case where a radiation imaging operation belonging to the same group as that of the radiation imaging operation is performed.

9. A non-transitory storage medium storing a computer program that causes a computer to execute a method for controlling a radiation imaging control apparatus configured to control a radiation imaging operation using a radiation generation apparatus in which a radiation generation condition is adjustable by a manual operation, the method comprising:
    setting the radiation generation condition for the radiation imaging operation;
    transmitting the radiation generation condition to the radiation generation apparatus; and
    limiting transmission of the radiation generation condition in a case where a radiation imaging operation belonging to the same group as that of the radiation imaging operation is performed.

* * * * *